US008992951B2

(12) United States Patent
Henry

(10) Patent No.: US 8,992,951 B2
(45) Date of Patent: *Mar. 31, 2015

(54) FORMULATIONS, PROCEDURES, METHODS AND COMBINATIONS THEREOF FOR REDUCING OR PREVENTING THE DEVELOPMENT, OR THE RISK OF DEVELOPMENT, OF NEUROPATHOLOGY AS A RESULT OF TRAUMA

(71) Applicant: James Lorne Henry, Burlington (CA)

(72) Inventor: James Lorne Henry, Burlington (CA)

(73) Assignee: Sapna Life Sciences Corporation, Burlington (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/815,716

(22) Filed: Mar. 15, 2013

(65) Prior Publication Data

US 2014/0193526 A1 Jul. 10, 2014

Related U.S. Application Data

(60) Provisional application No. 61/750,745, filed on Jan. 9, 2013.

(51) Int. Cl.
*A61K 9/00* (2006.01)
*A61K 38/00* (2006.01)
*A61P 25/02* (2006.01)
*A61K 33/14* (2006.01)
*A61K 31/19* (2006.01)
*A61K 31/194* (2006.01)
*A61K 31/195* (2006.01)
*A61K 31/197* (2006.01)
*A61K 31/495* (2006.01)
*A61K 31/496* (2006.01)
*A61K 31/5377* (2006.01)
*A61K 31/57* (2006.01)
*A61K 33/00* (2006.01)

(52) U.S. Cl.
CPC ............ *A61K 33/14* (2013.01); *A61K 31/19* (2010.12); *A61K 31/194* (2013.01); *A61K 31/195* (2013.01); *A61K 31/197* (2013.01); *A61K 31/495* (2013.01); *A61K 31/496* (2013.01); *A61K 31/5377* (2013.01); *A61K 31/57* (2013.01); *A61K 33/00* (2013.01)
USPC .......................................... 424/400; 514/18.2

(58) Field of Classification Search
None
See application file for complete search history.

(56) References Cited

U.S. PATENT DOCUMENTS

| 2003/0027817 A1 | 2/2003 | Tollefson |
| 2005/0004106 A1 | 1/2005 | Romano |
| 2008/0107756 A1 | 5/2008 | Satow |
| 2009/0203658 A1 | 8/2009 | Marx et al. |
| 2010/0316678 A1 | 12/2010 | Goodchild |
| 2011/0046090 A1 | 2/2011 | Barlow et al. |
| 2011/0288059 A1 | 11/2011 | Marx et al. |
| 2011/0301133 A1 | 12/2011 | Wu et al. |
| 2014/0193523 A1 | 7/2014 | Henry |
| 2014/0193526 A1 | 7/2014 | Henry |
| 2014/0193528 A1 | 7/2014 | Henry |
| 2014/0194397 A1 | 7/2014 | Henry |

FOREIGN PATENT DOCUMENTS

| CA | 2625210 A2 | 5/2007 |
| CA | 2831054 | 12/2013 |
| WO | 2009089024 A1 | 7/2009 |
| WO | 2010077680 A2 | 7/2010 |
| WO | 20100107815 A1 | 9/2010 |
| WO | 2012112340 A2 | 8/2012 |
| WO | 2014107794 A2 | 7/2014 |
| WO | 2014108807 A2 | 7/2014 |
| WO | 2014108808 A2 | 7/2014 |
| WO | 2014108809 A2 | 7/2014 |
| WO | 201414802 A2 | 9/2014 |

OTHER PUBLICATIONS

Drug Information Online, Aprepitant Side Effects, May 15, 2012, http://www.drugs.com/sfx/aprepitant-side-effects.html, pp. 1-3.*
International Search Report and Written Opinion of W02014/107794 dated May 6, 2014.
International Search Report and Written Opinion of WO2014/108809 dated Jul. 24, 2014.
International Search Report and Written Opinion of WO2014/108807 dated Aug. 22, 2014.
Schumacher, Michael et al., "Progesterone and progestins: neuroprotection and myelin repair", Current Opinion in Pharmacology 2008, pp. 740-746.
Freynhagen, R., et al., "Efficacy and Safety of Pregabalin in Treatment of Refractory Patients with Various Neuropathic Pain Entities in Clinical Routine", Int. J. Coin. Pract., 2007, 6212, pp. 1989-1996.

(Continued)

*Primary Examiner* — Trevor Love
(74) *Attorney, Agent, or Firm* — Bereskin & Parr LLP/S.E.N.C.R.L., s.r.l.; Patricia Folkins

(57) ABSTRACT

Novel formulations and methods for their use in treating neuropathology incident to trauma are provided. Multiple-component formulations of the invention, and especially those having four components, comprise biologically active compounds configured for preventing or reducing the incidence and severity of damage caused by neurotrauma. Formulations and methods of the invention effect both neuroprotective actions to prevent or reduce secondary injuries, and neurotrophic actions to repair and restore cells and tissues affected by the trauma. Formulations and methods of the invention are especially useful in treating neurological trauma, such as those caused by sports injuries and improvised explosive devices in combat.

41 Claims, No Drawings

(56) References Cited

OTHER PUBLICATIONS

International Search Report and Written Opinion for WO2014/108808 dated Jul. 23, 2014.
Alzheimer's Disease. Alzhiemer's Association Mar. 2011. www.alz.org.
Liu, Xishi et al., "Valproic Acid and Progestin Inhibit Lesion Growth and Reduce Hyperalgesia in Experimentally Induced Endometriosis in Rats", Journal of Obstetrics and Gynaecology Research, Jun. 2011.
Drug Information Online, Aprepitant Side Effects, May 15, 2012, http://www.drugs.com/sfx/aprepitant-side-effects.html., pp. 1-3.
International Search Report and Written Opinion of WO2014/140802 dated Oct. 8, 2014.
International Search Report and Written Opinion of WO2014/162195 dated Aug. 28, 2014.
Final Office Action dated Nov. 25, 2014 for U.S. Appl. No. 14/055,604.

* cited by examiner

FORMULATIONS, PROCEDURES, METHODS AND COMBINATIONS THEREOF FOR REDUCING OR PREVENTING THE DEVELOPMENT, OR THE RISK OF DEVELOPMENT, OF NEUROPATHOLOGY AS A RESULT OF TRAUMA

RELATED APPLICATION AND PRIORITY

This Utility patent application claims the priority and benefit of commonly owned U.S. Provisional Patent Application Ser. No. 61/750,745 of Henry, as filed 9 Jan. 2013, and as entitled "Formulations, Methods And Procedures For Reducing Or Preventing The Development Or The Risk Of Development Of Neuropathology As A Result Of Traumatic Injury" which provisional patent application is hereby incorporated by reference in its entirety into the present patent application.

FIELD OF THE INVENTION

The presently disclosed invention and many particular invention embodiments relate to multiple-component formulations, the use of such formulations, and to methods, procedures and combinations thereof to prevent or reduce, or to reduce the risk of, the damage that can otherwise lead to numerous types of neuropathology as a result of trauma.

BACKGROUND OF THE INVENTION

Trauma to neural tissue often leads to injury, dysfunction or death of cells and tissues, and thus to numerous adverse health conditions and disabilities. Such trauma includes damage to nerve cells, or to cells that support the healthy normal function and survival of nerve cells, and therefore includes damage to neural support cells, as well as to tissues that support the healthy, or normal, function and survival of nerve cells and tissues.

Injury to these cells and tissues typically occurs as a result of two factors. The first factor is the direct effect of the trauma itself. This is a primary type injury. The second factor results from biochemical cascades of cellular and metabolic processes that are activated or triggered directly by the trauma-induced tissue damage of the primary injury. The direct, or "primary," damage (such as physical disruption) is not preventable. However, in accordance with the presently disclosed novel formulations, procedures and methods, the indirect damage, which is typically considered a "secondary injury", or "secondary damage", can be reduced, ameliorated or prevented by the present therapeutic treatment, intervention and formulations, and is therefore regarded as a salvageable neuropathology.

In the context of the presently disclosed technology the term "trauma" means a wound, injury or damage to a mammalian body or body part, or a condition resulting from such a wound or injury. In one aspect, the presently disclosed technology is particularly applicable to a wound, injury or damage that includes, as examples, physical, chemical, metabolic, medical, surgical or any other injury or damage to any nerve or nerve cell, neural support cell or neural support tissue, whether in the central nervous system or in the periphery, as described herein.

In another aspect, the presently disclosed technology is particularly applicable to physical trauma induced by, for example but not exclusively, vehicle accidents, workplace accidents, sports injuries and accidents, falls, burns, radiation, battlefield injuries such as but not exclusive to concussive blast injuries and injuries from landmines or improvised explosive devices (IED's), penetrating injuries and the like but can occur as a result of any traumatic event.

The presently disclosed technology is also particularly applicable to chemical trauma induced by, for example but not exclusively, medication or medication overdose, drug or drug overdose, drug abuse (such as methylenedioxyamphetamine, or MDMA, and the like), alcohol overdose, stimulant drugs such as pentylenetetrazol, streptozotocin, carbon dioxide poisoning, carbon monoxide poisoning, heavy metals, acrylamide and related chemicals, overexposure to certain environmental chemicals such as copper or natural hazards such as scorpion venom toxin, herbicides, agricultural insecticides such as lindane, hazardous industrial chemicals, neurotoxin bioterrorism chemicals such as soman and sarin, radiation bioterrorism chemicals such as polonium and strontium, and the like.

As an additional advantage, the presently disclosed technology is particularly applicable to metabolic trauma induced by, as examples but not exclusively, hypoxia, central nervous system ischemia, peripheral ischemia, enteric nervous system ischemia, hypoperfusion of nerve tissue, multiple sclerosis, shingles (herpes zoster), pathogens, diabetes, diabetic shock, stroke, epileptic or other seizure, post-polio syndrome, HIV/AIDS peripheral neuropathic pain, subacute posttraumatic myelopathy, and other effects, syndromes and conditions following some type of trauma to the body or its nervous system. Metabolic trauma can also include but is not exclusive to hypoglycemia, hyperglycemia, ischemia, diabetic shock, epilepsy or seizure, hypoperfusion of nerve tissue during cardiac arrest, hypoperfusion in newborns resulting from complications at delivery and the like.

The presently disclosed technology is similarly applicable to trauma induced by medical treatment or procedure, for example but not exclusively, injections, inoculation, implants, antibiotics, biologic drugs, antibodies, chemotherapy (for example but not exclusively with methotrexate, cisplatin, cytosine arabinose, carmustine, thiotepa among others), radiation therapy, immunosuppressants (for example tacrolimus), and the like, or during a medical procedure that can reduce or impede the blood supply for any period of time and the like.

Trauma from surgery includes, as examples, laparoscopy, amputation, mastectomy, cesarean section, cardiac surgery, hernia repair, cholecystectomy, joint replacement, thoracotomy, reparative surgery or any case, condition or situation where there is or might be detectable or undetectable cut, wound, injury or damage to nerves, nerve cells, neural support cells or neural support tissues or where long-term outcome from surgery can include adverse health conditions or disability as, for example, with failed back syndrome.

Trauma, or "neurotrauma", to nerve cells, to neural support cells or to neural support tissues, can be, for example but not exclusively, traumatic brain injury (TBI), central nervous system ischemia, spinal cord injury, enteric nervous system injury, peripheral nerve injury or other type of injury to nerve cells.

Outcomes of traumatic damage to nerve cells or tissues differ significantly from the outcomes of traumatic damage to non-neural tissues and cells. Non-neural tissues repair relatively rapidly compared to nerves or nerve cells, and that repair often results in a damage site restored to nearly identical condition to the original (pre-trauma) state of the tissue, especially with respect to function. In stark contrast, trauma to neural tissue, such as nerves, nerve cells or any of the neural support cells or neural support tissues, often results in adverse health conditions or outcomes that persist for days, weeks or permanently. It is this set of disadvantageous characteristics and events regarding neural tissues to which the present invention is directed.

The severity and duration of such adverse outcomes resulting from neural tissue injury and cell death are governed by a balance of restorative, regenerative adaptive processes and destructive, degenerative maladaptive processes in those neural cells and tissues. In such injured cells and tissues, adaptive processes drive cells and tissues toward recovery and repair, and the restoration of pre-trauma function. During the same period, maladaptive processes drive cells and tissues toward loss of cell integrity and function, and even toward cell death. Effective control of the balance of adaptive and maladaptive processes following trauma to neural tissue has proven to be difficult. It is noteworthy that this balance is often skewed toward the maladaptive outcomes in neural tissue, such as cell or tissue death, and thus to permanent dysfunction and disability. Conventional medical and therapeutic systems and processes have shown little effectiveness in addressing these negative outcomes. There is therefore a significant clinical and societal need for new methods and formulations directed toward the treatment of secondary injury to neural tissues, such as nerve cells, neural support cells and neural support tissues that maintain the health and function of nerve cells. The scope and spirit of the many present invention embodiments are directed toward addressing this clinical and societal heretofore unsolved need by promoting natural adaptive processes while inhibiting intrinsic maladaptive processes, thereby reducing or preventing the development, or the risk of development, of neuropathology as a result of traumatic injury.

The present embodiments of the invention include, among other advantageous aspects, numerous formulations adapted and arranged for administration to a subject or patient in need thereof soon after that subject or patient has experienced a traumatic event. In another key aspect, some particular disclosed embodiments include formulations that may be used in preventative ways, such as when a traumatic event is likely, anticipated or possible. In a similar manner, some particular disclosed embodiments include formulations that may be used in prophylactic ways, such as in the case of a procedure about which incidence studies inform may lead to neuropathology.

In one significant aspect, the disclosed formulations comprise two or more pharmaceutically effective compounds, administered to a subject or patient in accordance with the pharmaceutical effectiveness of the components and amounts to be administered. In some embodiments, the relative timing of the administrations of the formulations is keyed to the context of the actual, possible or likely nature of the injury. Regarding the timing aspects, the embodiments of the invention can be practiced with respect to the time that the injury or disorder has occurred, or with respect to a possibility, a probability or a likelihood that an injury will occur in the impending future. Thus, in one aspect some embodiments can be adapted and arranged to preventive purposes or to prophylactic purposes or to curative purposes or to ameliorative purposes.

Embodiments of the invention can therefore be practiced within a rationalized earliest possible time frame following, or preceding, trauma, thereby to promote adaptive processes and to inhibit maladaptive processes activated by the trauma, or which are likely to be activated by the trauma. Thus, the present formulations, methods, and procedures are all directed toward reducing or preventing the development, or the risk of development, of secondary nerve cell damage, loss of function, or cell death.

In this same vein, the presently disclosed invention and its many embodiments address the critical facts that damage or injury to nerves, nerve cells, neural support cells and neural support tissues can be a result of trauma, but such damage or injury can also be secondary, due to a complex series of events or mechanisms often triggered by the direct injury. Disability arising from the primary injury occurring at the moment of the traumatic event, whether it is to brain, spinal cord, enteric nervous system or peripheral nervous system, is not preventable. However, disability resulting from such secondary injury is somewhat or completely preventable in the context of the invention. This prevention or amelioration is the object of the many presently disclosed invention embodiments. The presently disclosed invention and its embodiments comprise an intervention with a pharmaceutically appropriate additive or synergistic drug combination, given following trauma or in advance of expected or potential trauma, and administered by a route that provides access under the circumstances of the traumatic event. The scope and the spirit of the many presently disclosed embodiments of the technology are thus directed to promoting the naturally-occurring adaptive processes triggered by, and resulting from, the primary damage and to inhibit the naturally-occurring maladaptive processes triggered by the primary damage. Thus, the formulations, methods and procedures of the presently disclosed technology will reduce or prevent the development, or the risk of development, of neuropathology as a result of traumatic injury.

BRIEF DESCRIPTION OF THE INVENTION

The presently disclosed technology includes formulations, methods, procedures and combinations thereof directed toward reducing or preventing the development, or the risk of development, of neuropathology as a result of traumatic injury. Embodiments of the invention address heretofore unmet or unsolved medical needs including traumatic brain injury, central nervous system ischemia, spinal cord injury, enteric nervous system injury, peripheral nerve injury and any other injury that can include or affect nerve cells, neural support cells or neural support tissues.

These unmet or unsolved medical needs share the common aspect of the potential for life-long adverse health conditions or disability. They also share the commonality of the void in current medical interventions which attempt to reduce or prevent these adverse health conditions or disabilities. These conditions also share common mechanisms of the secondary injury that develops following a primary injury or trauma, common mechanisms that trigger or lead to this secondary injury. These conditions also share common possible therapeutic windows for inhibiting or promoting the cascades of mechanisms triggered by the primary injury. As such mechanisms are triggered immediately by trauma, while others temporally downstream in the cascades of biochemical and metabolic pathways are engaged at different times following trauma, it is necessary to administer the components comprising the formulation during the hours, days and in some cases, the weeks or months, following trauma, with immediate or earliest possible initiation of treatment of paramount importance for the preventive measures to arrest the maladaptive cascades and to promote the adaptive cascades, as well as continuation of practice according to need.

Trauma to the nervous system, or neurotrauma, which includes acquired nerve injury, is a catastrophic injury that imposes a number of negative outcomes that usually inflict one or more adverse health conditions or disabilities on its victims. These adverse health conditions and disabilities frequently place both short-term and long-term burdens on individuals, families, communities, the workplace, the health care system and economies in general. Few or no current practices are directed at attempts to lessen, prevent or ameliorate the effects of trauma on secondary injury. Until the presently disclosed formulations, methods and procedures, no satisfactory methods or pharmaceutical treatments have been successful at preventing or reducing the secondary injury, or neuropathology, associated with trauma and its sequalae.

The presently disclosed invention embodiments are based at least in some part upon Applicant's speculation that many of the negative outcomes and disabilities of trauma-induced neuropathology can be reduced in severity, or prevented altogether, by appropriate early intervention with one or more of the present methods, procedures and pharmaceutical formulations, especially when continued for a medically beneficial period of time. There are currently rehabilitation practices and interventions to treat or manage the disabilities that result from trauma to nerve cells and neural support cells once they have been established. However, immediate or early approaches targeted at the development phase of these outcomes are unknown, few or ineffective. Illustrative of the failings of the current "conventional" treatments are those provided at the time of a traumatic event, whereby conventional standard medical practice focuses on the treatment of immediate symptoms such as bleeding, or to avoid or prevent infection, and do not even recognize the advantages of the present invention. Disadvantageously, currently conventional medical practice does not recognize the advantages of treatment to promote the cascades of adaptive processes, or to prevent or reduce the cascades of maladaptive processes, which result from trauma and that lead to prolonged or permanent adverse health conditions and disability. It is this latter treatment modality, i.e., effecting treatment to prevent or reduce damage from the secondary sequalae, that the presently disclosed technology is directed.

The present disclosed technology presents and illustrates at least four particular advantageous aspects of the invention embodiments, together comprising formulations, methods and procedures for reducing or preventing the development or the risk of development of neuropathology as a result of traumatic injury.

One particular advantageous aspect of embodiments of the invention includes the formulations of the presently disclosed technology, which formulations comprise two or more pharmaceutical compounds from four families of chemical compounds, administered together or sequentially at clinically effective doses. In general, each chemical compound, or entity, in the formulation is theorized to target a different biological process or different biological processes that is or are involved in governing the degree of secondary injury that follows a primary traumatic injury. Alternatively stated, some components of the formulations are directed at optimizing or facilitating the adaptive processes that follow, or are triggered by, a primary traumatic injury. Some components of the formulation are directed at minimizing or inhibiting the maladaptive processes that follow or are triggered by a primary traumatic injury. As described herein, adaptive processes lead to recovery and, in contrast, maladaptive processes lead to tissue damage and cell death.

Before the present invention, the particular combinations of compounds described herein that make up or constitute the present formulations were unknown. Evidence of the efficaciousness of single-compound treatments for neuropathology is spotty or contradictory. Hindsight with respect to the field of neurotrauma hints only generally toward single-component remedies, and not to any particular combination of compounds to possibly be selected from the various categories of pharmaceuticals and myriad permutations possibly selectable from them. Nonetheless, Applicant has discovered that the formulations, methods and procedures of the presently disclosed invention are effective in reducing or preventing the development of, or the degree of, or the risk of development of, neuropathology as a result of trauma.

Despite the fact that single compound administrations in the art have had only limited, or no, beneficial effects, Applicant has found that a multi-drug approach that is directed at one or a plurality of adaptive and maladaptive processes, as is exemplified by the present formulations, have greater beneficial effects than those deriving from a single-compound approach.

A second particular advantageous aspect of the invention embodiments is the specific treatment modality, wherein a formulation of the invention is given in temporal relation as a preventive, prophylactic or posttraumatic event treatment. The preventive practice aspects of the present invention are in cases where there is a high risk of trauma to an individual or there is planned entry into a condition, situation or place where such high risk may ensue. Prophylactic practice of the invention is in cases where incidence studies inform that a procedure or practice results in neuropathology in a given number of subjects or patients. Posttraumatic event practice of the invention is in cases where a traumatic event has occurred or is occurring. In all cases, the presently disclosed technology is directed at preventing or reducing, or reducing the risk of, such secondary neuropathology as a result of trauma.

A third particular advantageous aspect of the methods and formulations of the invention embodiments is the timing and route of administration, coupling the formulations and the delivery to the means of administering a formulation in a time-effective practice. As one example, in the event of unanticipated trauma, which may occur away from a hospital/clinic setting, at-site immediate or earliest possible administration of the formulation can be by any fast and effective intervention in an easily and acceptable format. Delivery by intranasal administration may also be by nasal spray, or by any effective means and methods effective to address the specific trauma, or class or class of trauma. In the context of an event of an anticipated trauma, for example, one that occurs in a hospital/clinic setting, treatment with a formulation can be intranasal administration but can alternatively be by oral, buccal, intravenous or even intramuscular routes. Timing and route of administration of the formulations thus can be adapted and arranged to accommodate specific and unique conditions, situations, severity and type of trauma, and the status of the subject/recipient.

A fourth particular advantageous aspect of the invention embodiments directs the formulations, the methods and the procedures specifically at secondary injury resulting from any and all types of trauma. This aspect of the invention is in contrast to the conventional view that the spectrum of types of trauma to the nervous system is not typically or usually considered as a single medical issue. To illustrate this point, standard emergency or immediate treatment of traumatic brain injury and stroke are different and follow different standard protocols. However, while the primary trauma may be different, the processes and mechanisms of the secondary injury that can and often do ensue from both conditions share common processes. Traumatic brain injury and stroke are thought to trigger the same adaptive mechanisms and, similarly, they both trigger the same maladaptive mechanisms. Advantageously, treatment by the present means and methods could be the same or similar for both stroke and TBI. The present fourth particular advantageous aspect of the invention embodiments is in some respect that the formulations, methods and procedures can be applied universally or broadly for many types of trauma to the nervous system. As examples, practice of the invention is the same or similar for metabolic trauma, such as from an epileptic seizure, and for impact or concussion trauma, such as from a penetrating head wound; similarly, trauma from chemotherapy or radiation therapy is believed to trigger the same neuropathological processes. Further, trauma is treated with the same practices of the invention whether trauma is to the periphery, to the enteric nervous system or to the central nervous system. Treating trauma-induced neuropathology as a single entity presents the framework, then, for practice of the present invention to fill the gap between standard emergency practice and standard rehabilitation practice, as described herein.

There is an additional aspect, or advantage, of the presently disclosed invention embodiments. Because trauma to the brain is known to increase the risk of the later development of some degenerative disorders, the presently disclosed technology is also directed at reducing or preventing the risk of longer-term neurodegeneration. To substantiate this point, head trauma is a risk factor for Parkinson's disease; stroke is a risk factor for Alzheimer's disease. As detailed herein, neuropathology as a result of trauma occurs as cascades of progressing adaptive and maladaptive processes that alter the health, function and survival of nerves, nerve cells, neural support cells and neural support tissues, and, as these cascades are shared by trauma of different types the presently disclosed formulations, methods and procedures are useful in reducing risk factors for neurodegenerative diseases.

SUMMARY OF THE INVENTION

The presently disclosed many embodiments of the invention include formulations, methods, procedures and means for treating any neuropathological condition that is caused, at least partially, by trauma of any kind and involves endogenous processes or biosynthetic and metabolic pathways that govern, regulate or influence the health or function of nerves or nerve cells, or cells or tissues upon which nerves or nerve cells depend to maintain health and function. Conditions of trauma are known to activate or trigger such processes and pathways that protect or restore health of nerves and nerve cells, as well as such processes and pathways that lead to loss of function, further damage and even cell death of nerves, nerve cells, neural support cells and neural support tissues. It is the balance of these protective versus destructive processes and pathways that governs and determines disability outcome.

Particular compounds that comprise the formulations are any two, any three or all four of an anticonvulsant, a neurosteroid, an NK-1 receptor antagonist and a lithium drug or an analog, and these may be administered to or given to a subject in need in any combination. In some preferred embodiments of the invention the anticonvulsant can be gabapentin, the neurosteroid can be progesterone, the NK-1 receptor antagonist can be aprepitant and the lithium drug can be lithium carbonate. An analog is a compound that is a modification of the original drug or enhances the availability of the drug or provides a slow release, a delayed release or a controlled release of the drug for the target but still modifies the pathway similar to the parent compound. As a person having ordinary skill in the art will appreciate, any formulations of compounds that promote or inhibit endogenous processes that are activated by trauma and that are involved in the repair or in the injury to nerves or nerve cells are within the spirit and scope of the presently disclosed invention embodiments.

In the context of the presently disclosed technology the term "formulation" means a combination or mixture of pharmaceutically active or effective chemical entities in respective pharmaceutically effective doses, to create a desired end drug product, in such a form that it can be safely administered to, given to, or taken by, a subject, and may include other ingredients or substances. Examples of such other ingredients or substances include, as examples, but not limited to, excipients, buffers, penetration enhancers, stabilizers, absorption enhancers and carriers.

Further, chemical entities in the formulations of the presently disclosed technology can include any pro-drug, derivative, metabolite, analog, salt or any other form including natural, standard or slow-, delayed-, sequential- or controlled-release forms.

Even further, the formulations may be delivered in any form, for example, as a tablet, capsule, pill, spray, solution, paste, cream or any standard way of administering a drug. Formulations may be delivered in any way that controls the release of the formulation.

Components of the formulations can be given together as a single dose or sequentially in any order as needed or advisable for a particular trauma to a particular subject, such as a particular human.

In embodiments of the invention utilizing such two or more of compounds, the targets can include any target or targets that activate, enhance or facilitate processes or pathways that promote health and function of nerves and nerve cells, and the targets can include any target or targets that inhibit, attenuate or interfere with processes or pathways that lead to loss of function, injury, damage or death of nerves or nerve cells. Loss of function or injury, damage or cell death can also include that to neural support cells or neural support tissues. Depending on the specific use and therapeutic context, analogues or modifications to the specific compounds included in embodiments of this invention can be tailored to target specific biological processes or pathways or to facilitate access of compounds to target sites in the central, peripheral or enteric nervous systems.

Delivery of compounds of embodiments of the invention, and in accordance with the methods and procedures described herein, can be effected in any manner that results in delivery of the compounds of embodiments of the invention such that positive or negative influence on the target pathway is accomplished. For example, the formulations can be administered by one or more routes such as, but not limited to oral, buccal, mucosal, parenteral, rectal, sub-cutaneous, transdermal, topical, intravenous, intrathecal, intravaginal, nasal, nasal inhalation, pulmonary inhalation, iontophoresis through the skin, iontophoresis through mucosal or buccal membranes, dermal patch, epidural, intracranial, intrathecal, intrapharyngeal, sublingual, intra-articular, intramuscular and subcutaneous.

In the context of invention embodiments the term "neural support cell" is any cell that supports or could be considered to support the health, normal function, phenotype, gene expression and survival of nerves and nerve cells, and include, as examples but not exclusively, glial cells, microglia, myelin cells, astroglia, oligodendrocytes, satellite cells, Schwann cells, vascular endothelial cells, gastric epithelial cells, interstitial cells of Cajal, and the like.

In the context of invention embodiments the term "neural support tissue" is any tissue that supports or could be considered to support the health, normal function, phenotype, normal gene expression or survival of nerves, nerve cells or neural support cells, and include, as examples but not exclusively, cells of the vasculature or microvasculature, particularly the endothelial cells that prevent blood from leaking into nerve tissue and that provide the selective blood-nerve and blood-brain barrier that allows the passage of certain supportive chemicals into nerve tissue as well as the passage of nerve tissue wastes out of nerve tissue, as well as epithelial cells and interstitial cells of Cajal of the gut.

Preferably the administered compounds selected will facilitate, promote or potentiate adaptive responses to trauma, and will interfere with, lessen or inhibit maladaptive processes. This can occur, for example, by binding to an enzyme, receptor, allosteric site or other step of an endogenous biochemical or biosynthetic pathway to the extent that such pathway is altered, enabled, allowed or facilitated in its effective functioning, as in the case of adaptive processes, or would prevent or lessen its effective functioning, as in the case of maladaptive processes.

The presently disclosed invention and its embodiments are useful for strengthening or improving natural processes that help to restore the health and function of nerves, nerve cells, neural support cells and neural support tissues when compromised by trauma. Further, the presently disclosed invention embodiments are also useful for lessening, diminishing or inhibiting natural processes that lead to loss of health and function of nerves, nerve cells, neural support cells and neural support tissues when caused by trauma.

As one of ordinary skill in the art will comprehend, appropriate dosages of compounds according to the various embodiments of the invention can vary widely depending, inter alia, upon the type of trauma or condition to be treated, the route of treatment, the subject mammal, the sequalae of mechanisms and processes to be controlled, the compounds involved, and the like. Dosages range greatly, for example, between 10 nanograms and 60 grams per kilogram of body weight of the individual mammal. Some typical ranges for the amount of an anti-convulsant such as gabapentin would include 5 to 9,600 mg as an acceptable range, 50 to 4,800 mg as a preferable range, 100 to 2,400 mg as a more preferable range and 200 to 600 mg as a most preferable range. Some typical ranges for the amount of a neurosteroid such as progesterone would include 0.05 to 1,200 mg as an acceptable range, 5 to 600 mg as a preferable range, 50 to 450 mg as a more preferable range and 100 to 300 mg as a most preferable range. Some typical ranges for the amount of an NK-1 receptor antagonist such as aprepitant would include 0.05 to 750 mg as an acceptable range, 5 to 375 mg as a preferable range, 20 to 250 as a more preferable range and 40 to 120 mg as a most preferable range. Some typical ranges for the amount of lithium, for example lithium carbonate, would include 0.5 to 3,600 mg as an acceptable range, 30 to 1,800 mg as a preferable range, 100 to 900 mg as a more preferable range and 200 to 600 mg as a most preferable range. As a person of skill in the art will understand dosages would be arranged and adapted depending on the need, the individual, the severity of the trauma, the response to administration of the formulation, the time to treatment before or after a traumatic event, the situation, whether in the field or in a hospital, and the like.

In some embodiments of the invention, mammals, and especially humans, are suitable subjects. Of course, other mammals, such as cows, horses, cats, dogs, sheep, pigs and rodents, are suitable subjects for the presently disclosed invention embodiments.

1. Neuropathology

In the context of describing the invention, the terminology "Neuropathology" includes neuropathy, neurodegeneration and other effects of trauma on nerve cells, neural support cells and neural support tissues as defined herein. Neuropathology following trauma can occur in the brain, brainstem, cerebellum or spinal cord, in the enteric nervous system of the gut and in peripheral sensory, motor and autonomic nerves. Neuropathology is also influenced by events that impact neural support cells and neural support tissues, as neuron/glial interactions are important in brain homeostasis and are vital for survival of neurons in health as well as after brain injury and nerve cells require an adequate supply of oxygen and glucose from the vascular supply, and an adequate removal of cellular waste products by the vascular supply. As one example, injury-induced loss of glial cells or loss of glial function has been reported to have a negative outcome on injured neurons.

As a person having ordinary skill in the art will understand, pharmaceutical compositions, methods, procedures and means of administration of the presently disclosed invention are useful for treating or preventing any type of neuropathology such as, but not limited to, those characterized as traumatic brain injury, central nervous system ischemia, spinal cord injury, enteric nervous system injury and peripheral nerve injury as described herein. Also included among the many conditions that can be treated or prevented by the pharmaceutical compositions, methods and procedures of the presently disclosed invention are disturbances of any etiology so long as involvement of any process or pathway that can be modified or altered by gabapentin, progesterone, aprepitant or lithium, or any analog, derivative or related compound is present.

2. Manifestations of Neuropathology

Traumatic brain injury is a major public health issue, inter alia, because it is a leading cause of disability. Traumatic brain injury occurs commonly from falls, motor vehicle accidents, sports injuries and accidents, workplace accidents, other accidents, and explosions, as well as in warfare, but damage to the brain can also be inflicted by chemical, surgical, metabolic and other types of trauma as described herein. Repeated minor symptomatic or asymptomatic concussions and injuries to the brain have a cumulative effect that can be expressed as recurring headaches, periods of short term memory loss, depression, and appear, for example, as dementia pugilistica, posttraumatic stress disorder, chronic traumatic encephalopathy and similar disorders. Traumatic brain injury can also be caused, as one example, in patients with cancer who receive cancer drug therapies, which can result in complications including, among others, posterior reversible encephalopathy syndrome, cognitive dysfunction and the like. As another example, therapeutic radiation also can lead to brain injury; white matter necrosis occurs at doses of >60 Gy, leading to functional deficits including impairments in memory, attention and executive function, with profound effects on quality of life. Whether the numbers are large, as in the case of battlefield traumatic brain injury, or small, as with shaken baby syndrome, traumatic brain injury can be devastating to the individual.

Central nervous system ischemia is that condition when the blood supply or circulation to the brain, the brainstem, the cerebellum or the spinal cord is reduced. CNS ischemia may result from any reduction, restriction, interference or slowing of the blood circulation. Central nervous system ischemia can be focal or global. Cerebral ischemia alone is one of the leading causes of long-term disability; a recent review reports an estimated 700,000 cases of ischemic stroke in the US each year. When the normal blood supply to central nervous system tissue is occluded, or blocked, by a clot this is called a thrombotic stroke. In cases where a clot has been dislodged or broken off elsewhere in the circulation this is called an embolic stroke, such as the cerebral injury that occurs, for example, during surgical transcatheter aortic valve implantation. Brainstem, or cerebellar or spinal ischemia can result from surgical procedures, for example by aortic cross clamping during cardiac surgery, or as a result of hypoperfusion during cardiac arrest, or in newborns, as a result of temporary or prolonged hypoperfusion due to complications at delivery. Whether the numbers are large, as in the case of stroke, or small, as in the case of embolism from transcatheter aortic valve implantation, cerebral ischemia can have devastating outcomes for the individual.

Spinal cord injury has a severe impact on individual victims, on the healthcare system and on the economy, as evidenced from epidemiological studies and professional reports. A recent systematic review indicated that an estimated 40 million people worldwide suffer a spinal cord injury every year, and that most are young men. Of the new cases of spinal cord injury each year in the U.S., it has been reported that motor vehicle crashes account for 40% of spinal injuries, falls account for 28% and acts of violence such as gunshot or other wounds account for 15%. Sports injuries account for 8%, with another 9% of unreported or unknown causes. Whether the numbers are large, as in the case of vehicular accidents, or small, as in the case of many of the unreported cases, spinal cord injury can have a damaging outcome for the individual.

The enteric nervous system is vulnerable to trauma, including ischemia, chemical and inflammatory trauma, physical trauma such as puncture wounds, parasitic and amoeboid infection, and radiation, among other types of trauma. Many of the adverse health conditions and disability that result from enteric nervous system injury are due to secondary injury processes. As examples, chemotherapy and radiation therapy can lead to dysfunction and even cell death in the gastrointestinal tract. Bariatric surgery is associated with a number of neurological complications attributed to effector mechanisms besides changes in nutritional state, and may be associated with peripheral neuropathy, myelopathy, radiculoneuropathy and even encephalopathy. Many types of parasitic and amoeboid infiltrations, including salmonella, rotavirus, and many other bacterial, viral, and protozoan organisms, selectively produce neurotoxicity to enteric neuron cells, neural support cells and neural support tissues. Secondary injury to the enteric nervous system can have life-changing effects on the individual victim.

Neuropathology or neuropathy of peripheral nerves results in a myriad of adverse health conditions and disability. Neuropathic pain is perhaps the best documented, largely because of the enormous impact of chronic neuropathic pain on individuals and the fact that it tends to be refractory to medical treatment. However, other outcomes of secondary injury to peripheral nerves can be similarly devastating, including, in terms of sensory disturbance, numbness, dysesthesia (an unpleasant abnormal sensation, whether spontaneous or evoked), paresthesia (an abnormal sensation, such as tingling, whether spontaneous or evoked), hypoesthesia (decreased sensitivity to stimulation, excluding the special senses) and loss of proprioception (contributing to altered gait and to falls). In terms of motor control, peripheral neuropathy can lead to weakness, loss of movement, loss of corrective motor control and loss of muscle mass. Neuropathy of the autonomic nervous system can manifest as orthostatic hypotension, dysautonomia, altered sudomotor function, and the like. Whether the numbers are large, as those resulting from car accidents, or small, such as those resulting from laparoscopic surgery, the result of peripheral nerve injury can be a future of constant burning, debilitating neuropathic pain and any of these other adverse health conditions described herein.

There is an additional aspect, or advantage, of the present invention. For example, as trauma to the brain is known to increase the risk of the later development of some degenerative disorders, the presently disclosed technology is also directed at reducing or preventing the risk of longer-term neurodegeneration. Head trauma is a medically known risk factor for Parkinson's disease; stroke is a medically known risk factor for Alzheimer's disease. Further, slow degenerative disease is suspected in many athletes who have undergone multiple head traumas, such as in football, hockey and boxing; this manifests as mood swings, depression and forgetfulness that develop in football players years after retirement from the sport. Applicant posits that these manifestations of head trauma can be prevented or reduced by application or practice of the presently disclosed technology. Some victims of head trauma or repeated concussions or minor head injuries are driven to suicide. Applicant posits that at least some of these suicides may be prevented by application or practice of the presently disclosed technology, according to the methods and practices described herein.

Another striking example of progressive or developing neurodegeneration includes posttraumatic stress disorder that develops in soldiers weeks or even months after serving active duty. In 2012 more soldiers died from suicide than were killed in combat in Afghanistan: 349 died from suicide, 295 died in combat. Applicant posits as well that at least some suicides in military personnel may be prevented by application or practice of the presently disclosed technology, according to the methods and practices described herein.

3. Secondary Injury

The pathological changes, and the mechanisms or processes of secondary injury are shared by traumatic brain injury, central nervous system ischemia, spinal cord injury, peripheral nervous system injury and enteric nervous system injury. The many embodiments of the presently disclosed invention are directed at preventing or reducing the development of the sequalae of negative effects and symptoms that incidence studies indicate follow any of these types of trauma, and that can continue for months or years, or even permanently.

Parenthetically, in the context of the presently disclosed invention embodiments, prevention does not imply avoidance. Prevention in the context of avoidance would be, as examples, avoiding falls, wearing body armor, wearing seat belts, wearing helmets while bicycling, and the like. Prevention in the context of the presently disclosed invention embodiments is administration of a pharmaceutically effective dose of a formulation of two or more chemical entities, following methods, procedures and practices with the objective to reduce or prevent secondary injury by inhibiting or interfering with the natural maladaptive processes triggered by trauma and to promote recovery and repair by enhancing or promoting the natural adaptive processes triggered by this same trauma.

Secondary injury is triggered immediately or within hours, days, weeks, or even months, of the primary injury and can continue and progress over a prolonged period of time. This secondary injury is caused by cascades of parallel as well as consecutive pathological processes initiated at the moment of the trauma, often or usually with delayed clinical presentation. Secondary injury is the result of cellular, metabolic and neurochemical processes that are triggered by the primary injury but that continue over the hours, days, weeks and even months following trauma. In the context of the present invention embodiments injury processes are targets for pharmaceutical intervention with the formulations of the presently disclosed technology.

In addition to any physical damage, trauma also compromises the normal supply of oxygen and glucose to the nervous system. In turn, this causes a loss of ionic balance. These typically occur within several minutes of trauma.

Nerve cells do not store alternate sources of energy for cellular metabolism and therefore intracellular stores of adenosine triphosphate (ATP), the source of cellular energy, become rapidly depleted. Oxygen is required to generate sufficient ATP by oxidative phosphorylation. In particular, the enzyme, sodium/potassium ATPase, in the membrane of nerve cells is estimated to consume 70% of the energy supplied. ATPase maintains the sodium/potassium pump that maintains high intracellular potassium and low intracellular sodium. ATP depletion leads to multiple cascades of metabolic and biochemical processes, each of which follows a specific time course, including release of toxic levels of excitatory amino acids, ionic imbalance and acidotoxicity, oxidative stress, nitrative stress, inflammation, apoptosis, nerve terminal depolarization and necrosis. All lead to cell death, including death of nerve cells, neural support cells and neural support tissues. Endothelial cells comprise the walls of the vasculature and their death can lead to subsequent loss of integrity of vessel wall, infiltration of degradative chemicals and immune cells into neural tissue, as well as bleeding into the extravascular space.

When ATP is no longer available, the membrane polarization is lost and intracellularly stored transmitters exit along their concentration gradient. In particular, the excitatory amino acid transmitter, glutamate, is released at toxic levels, creating excitotoxicity. Among the receptors upon which glutamate acts is the N-methyl-D-aspartate (NMDA) receptor. Activation of this receptor leads to further depolarization through influx of sodium as well as calcium into the cell. Increased intracellular calcium leads to a further calcium release from intracellular stores.

There is also a calcium pump in the neuron cell membrane that normally maintains low intracellular calcium. A calcium ATPase in neuronal cell membranes governs this calcium pump. When the calcium pump ceases due to insufficient ATP, intracellular calcium rises even further. As a result of the influx of calcium through the NMDA receptor as well as by loss of the calcium pump combined with the release of intracellular calcium there is a massive activation of calcium-dependent proteases, lipases and DNAses, causing cells to die by their own catabolism.

Oxidative and nitrative stress spread from an injury zone into surrounding and even remote brain areas. Oxidative and nitrative stress are linked to activation of poly(ADP-ribose) polymerase, which, at high levels, impairs anaerobic glycolysis and mitochondrial respiration, leading to further exhaustion of ATP, energy failure and cell death. As a result, secondary injury can progress to nerve cells, neural support cells and neural support tissues beyond the locus of the primary injury and can include even areas remote from the site of this primary injury.

Secondary injury thus spreads both temporally and spatially. The negative sequalae may not manifest for weeks, months or years; suicide in athletes and soldiers years after trauma is one example. However, the optimal time to treat is as soon as possible or even before, around the time of trauma. Much of the neuropathology that is allowed to develop after the first few days may be refractory to any later medical treatment.

4. Need to Address the Complexity of Theorized Underlying Processes

In one aspect, the presently disclosed technology is based particularly on a polypharmacy, or a multi-drug, approach wherein delivery of beneficial chemical entities is given at specific times following or even before trauma. Earlier (conventional) approaches to treat trauma-induced neuropathology have heretofore focused exclusively on single drug approaches. Further, earlier approaches to treat trauma-induced neuropathology have focused uniquely on either adaptive processes or maladaptive processes. Even further, there is reticence to initiate clinical trials due to the complexity and cost demanded by treating a number of independent injury factors simultaneously that occur over a prolonged period of time following trauma. Applicant posits that efforts to develop effective therapeutic approaches to minimize negative sequalae of trauma have failed because of failure to accommodate the complexity of the events triggered by trauma and a failure to match this complexity with appropriate additive or synergistic multi-drug approaches. The presently disclosed technology and its embodiments are directed to address this unsolved need by evidence-based potentially synergistic formulations that promote recovery and restoration and at the same time inhibit or prevent loss of cell function and cell death.

Applicant posits further that due to the progressive nature of these cascades of events in secondary injury, these processes are accessible to, and available for, clinical intervention, and allow the development of new treatments to reduce or prevent the development of secondary injury triggered by traumatic events.

Any traumatic injury results in a localized initial direct damage accompanied by impaired regulation of blood flow and metabolism, usually with an ensuing edema swelling. Direct physical damage to nerve cells, neural support cells and neural support tissues can result, for example, from tearing, shearing, stretching or compression of nervous tissue. These events triggered directly by the traumatic event are usually treated clinically by hypothermia and efforts to reduce blood pressure as well as pharmacologically with drugs such as mannitol and barbiturates, largely to decrease mortality. What is not included in standard practice is effort or action to prevent or reduce the secondary injury resulting form the initial trauma. Standard immediate treatment of traumatic injury does not typically include steps to reduce or prevent or alter the plethora of secondary injury mechanisms that are triggered within minutes and hours of a traumatic event.

Some processes of secondary injury are activated immediately by a traumatic even. Some progress over a limited period of time and then return to pre-injury levels, while other processes may continue for days, weeks or months. Some processes are cascades, with one step triggering a subsequent step or subsequent steps. It is important to point out that once the initial processes have been completed any medical interventions for the treatment of the persisting adverse outcomes of traumatic injury are largely without benefit. As a result, from the time of a traumatic event there is a closing window of opportunity to reduce or prevent the development or the risk of development of neuropathology as a result of traumatic injury and that there is a platinum hour, a golden day and a silver week of opportunity to achieve optimal outcomes.

5. Secondary Injury as an Unaddressed Crisis

Unfortunately for those who are victims of trauma-induced neuropathology, standard immediate treatment strategies do not include neuroprotection. Immediate pre-hospital management of trauma focuses on airway clearance, prevention of hypoxia, hypercapnia and hypotension, as well as rapid transport to a medical center for detailed diagnosis and treatment. Actions to limit or prevent secondary injury to nerves, nerve cells or neural support cells or neural support tissues are absent from standard pre-hospital practice. For example, in a recent review, while a stated purpose of the report was to focus on limiting secondary brain injury, there was no reference to direct approaches to limit neuropathology from secondary injury; the focus was on emergency services without any regard for neuroprotection.

As a further example, in a recent report based on 119 cases of traumatic brain injury to 119 military personnel injured by anti-personnel devices or by vehicle landmines, specific recommendations were made based on the outcomes of various management approaches, including immediate battlefield management as well as subsequent hospital management. There was no recommendation for any action or procedure to provide neuroprotection from secondary brain injury resulting from the trauma. Similarly, recent recommendations for medical management following improvised explosive device accidents did not include any action or procedure to provide neuroprotection from secondary injury.

Clinical treatment of penetrating traumatic brain injury, as yet another example, typically consists of reducing increased intracranial pressure and reducing brain edema through surgical decompression, removal of any foreign bodies, administration of osmotic agents and reducing body temperature. Immediate standard treatment does not include steps to reduce or prevent the developing secondary injury.

In the case of spinal injury, immediate medical practice includes surgical decompression and stabilization in order to reduce edema and to prevent further primary injury. However, a retrospective observational study concluded that surgical treatment has not resulted in improved hospital mortality or length of stay and a consensus meeting concluded that surgery does not improve neurological outcome. Clearly, current standard practice is not meeting need. With 1200 new cases of spinal cord injury in the US each year, there is an urgent medical need to minimize the impact of injury on victims, on the healthcare system and on the economy.

Standard practice for trauma of any type, then, does not include steps or actions to minimize secondary injury. The result in many cases is unnecessary disability. Applicant posits that secondary injury can be prevented or reduced. Further, Applicant posits that the incidence and the severity of disability can also be prevented or reduced by including in standard emergency practice application and practice of the presently disclosed technology.

6. Addressing Unsolved and Unaddressed Needs

Incidence studies indicate the number of people in a population who will go on to develop disability following trauma of any given type. Until the presently disclosed invention, these numbers have been accepted as being inevitable. There is a general acceptance that disability results from trauma. Medical attention has not typically been directed at reducing these numbers, or preventing them altogether. Yet, as described herein much of the disability that ensues as a result of trauma is brought about by processes, largely biochemical, which can be modified by appropriate pharmaceutical intervention. Trauma-induced disability can thus be considered an unsolved need. Applicant posits that the number of people who go on to develop disability following trauma can be reduced. Further, Applicant posits that the severity of disability of those that do develop some level of disability can be reduced. The scope and the spirit of the presently disclosed invention embodiments are directed toward this unsolved need, both by reducing the number of victims of trauma that go on to develop adverse health conditions and disability, as well as by reducing the severity of disability in those who are left with trauma-induced negative health conditions. In accordance with this and other objects, the presently disclosed technology, in certain specific embodiments, aims to prevent or reduce the development, or the risk of development, of neuropathology that results from traumatic injury.

Numerous approaches have been taken to understand the variety of different mechanisms of secondary injury in both human and animal studies. With respect to drug therapy the literature contains several reviews of the area in the past few years. However, a consensus in these reviews is that despite at least 20 compounds being tested in over 50 trials by the year 2004, and over 30 phase III prospective clinical trials by 2010, significant endpoints have not been reached by any therapeutic intervention and no effective drug therapy is currently available. This failure can be attributed to a number of causes; even if a drug passes phase III clinical trials, full benefit may be elusive because all drugs currently in clinical trials II and III are monotherapies and do not address the consensus of the thought leaders in the field that the complexity of mechanisms contributing to secondary injury require a polypharmacy, or multi-drug, approach. The critical literature attributes much of the failure to bring effective interventions forward from phase III clinical trials to the fact that most such trials, and their antecedent development strategies, are directed at a single factor or mechanism, despite the awareness of the complexity of the underlying mechanisms.

Further, mechanisms leading to this injury and its ensuing disability are complex and occur over a period of time extending up to months after the traumatic event. Consensus opinion in the field is that a multi-mechanistic approach is needed, where multiple active compounds are given simultaneously or synchronously over specified respective periods of time. This is in stark contrast to the protocols of current clinical trials; these are based on monotherapies directed at only a limited number of the plethora of mechanisms that govern the severity of neuropathology and therefore the incidence and severity of the disability sequalae.

Applicant believes that at present, current drug development does not address the complexities of treatment that are needed and, further, that standard practice that is immediate and even rehabilitation standard practice totally misses the underlying fact that there is a "platinum hour," a "golden day" and a "silver week," when the adverse health conditions, and the disability resulting from trauma-induced neuropathology, can be reduced or prevented and that a multi-drug approach is needed.

Unexpectedly, Applicant has recognized the significance of the heretofore unknown possible synergy of selected combinations of compounds that include formulations of two, three or four compounds from the four categories of anticonvulsants, neurosteroids, NK-1 receptor antagonists and lithium-containing compounds. These combinations are adapted and arranged, and adaptable and arrangeable, to facilitate, promote or potentiate the adaptive processes that lead to neurological recovery, while at the same time lessening, or inhibiting, the maladaptive processes that lead to secondary, progressive tissue damage and cell death.

While the bases for the possible synergistic advantages of the present formulations have been heretofore unknown, as have been the present combinations, the formulations are directed toward modifying both adaptive and maladaptive processes. Embodiments of the invention are directed with the proposition that improved neurological outcomes that are known to result from trauma can be reduced or prevented, or the risk of such outcomes, can be reduced or prevented by the administration of a formulation of possibly synergistic compounds that combine neurotrophic actions that repair and restore, as well as neuroprotective actions that prevent or reduce secondary injury or damage.

Applicant posits that three important issues need to be addressed in order to arrive at effective medical intervention that will optimally reduce or prevent secondary brain injury resulting from brain or head trauma. One issue is the target or targets at which an intervention is aimed. Optimally, effective therapeutic intervention would promote, facilitate or potentiate restorative or regenerative targets, and will also inhibit, lessen or block destructive or degenerative targets involved in further injury, loss of function and cell death. A second issue is that, given the complexity of the biochemical, metabolic and cellular mechanisms causing secondary brain injury, multiple targets need to be included in any optimally effective therapeutic intervention. The third is that, given the temporal dispersal of the cascade of biochemical, metabolic and cellular events, the timing of various components of the intervention is critical, as well as the sequencing of the multiple therapeutic interventions. These three issues are addressed in the presently disclosed technology, which, along with its embodiments, includes evidence-based formulations, methods and procedures to reduce or prevent the development or the risk of development of neuropathology as a result of traumatic injury.

All types of trauma are known to activate secondary injury mechanisms. These secondary injury mechanisms are brought about as the outcome of a balance of adaptive and maladaptive biochemical and other processes triggered by trauma. The biochemical nature of these processes provides inroads to pharmaceutical intervention that can reduce or even prevent the alteration of function and even the death of nerve cells and their neural support cells and neural support tissues, alterations that can and often do ultimately lead to adverse health conditions or disability. The presently disclosed technology, in its numerous embodiments, is directed to promote these adaptive processes and to inhibit these maladaptive processes by specific pharmaceutical intervention at appropriate doses, with specific timings and sequences of intervention, using specific routes and modes of delivery.

Many traumatic events are unexpected and unanticipated such as sports concussions and battlefield injuries to the head. However, in many cases traumatic events can be anticipated, events that can and often do lead to adverse health conditions and disability. For example, clinical and incidence studies provide supportive evidence that as a result of certain procedures or events there is a high incidence of such adverse health conditions and disability. A person having ordinary skill in the art will recognize that prophylactic measures can be taken in conditions where there is a high enough possibility of neuropathology resulting from a clinical procedure. Further, in situations or conditions where a traumatic event may occur that can lead to damage or injury to nerve cells, to neural support cells or to neural support tissues, that precautionary or preventive measures are warranted, as described herein. The scope and spirit of the presently disclosed technology and its embodiments are directed toward both: unanticipated as well as anticipated traumatic injury.

Some examples are provided to illustrate what is meant as anticipated and unanticipated traumatic events. Minor head injury events are usually unanticipated, and have been reported to lead to restrictions in lifestyle one year later in 47% of admissions to hospital. Chronic pain caused by surgery varies according to the type of surgery, but continuing pain one year after amputation has been reported in up to 85% of patients. Further, medically induced sensory, motor, autonomic or enteric nerve damage can and often does occur as a result of chemotherapy or radiation therapy. Spinal cord injury is usually unanticipated, and survivors can be expected to have permanent physical disabilities, reduced independence, serious medical complications and enormous financial burden. Stroke is usually unanticipated, but in view of the fact that an estimated 44 million disability-adjusted life-years are lost by stroke survivors worldwide, many who have had a stroke know that they are at risk of a subsequent stroke or subsequent strokes. Applicant posits that much of the adverse health conditions and disability resulting from these and all traumas are amenable to therapeutic intervention.

As described herein, each of the chemical entities in a formulation of embodiments of the invention is theorized to target one or more biological processes or mechanisms. Applicant theorizes that some of these mechanisms may sometimes be involved in governing the incidence and the degree or severity of secondary injury that follows the primary traumatic injury. It is at this secondary injury to which the formulations of the invention embodiments are directed. A great amount of investigation regarding individual members of these categories has produced no efficacious formulations or methods. Indeed, a great amount of research in the field of neuropathology does not support aspects of Applicant's theory regarding the efficacy of particular combinations and dosages of these categories of compounds. This is so especially because, in some cases, administration of a single compound seldom produces adequate benefit, if any, and sometimes causes harm.

Despite this, Applicant presents novel formulations and methods having utility in treating various types and forms of neuropathology. In some sense, selected literature in the field might support the view that some of the individual compounds discussed herein, such as the neurosteroids and lithium-containing drugs, would be effective in promoting, facilitating or potentiating adaptive processes due to, or resulting from, trauma. In a similar sense, selected literature in the field might support the view that some anticonvulsants, some of the NK-1 receptor antagonists and some lithium-containing drugs, might act to minimize or inhibit maladaptive processes that follow or are triggered by a primary traumatic injury. Again, attempts at using these compounds have failed to provide sufficiently efficacious solutions to neuropathological conditions, although some single-compound attempts have shown some benefit.

Applicant has recognized the significance of the heretofore unknown complementarity of selected combinations of compounds that include formulations of two, three or four compounds from the four categories of anticonvulsants, neurosteroids, NK-1 receptor antagonists and lithium-containing compounds. These combinations are adapted and arranged, and adaptable and arrangeable, to facilitate, promote or potentiate the adaptive processes that lead to neurological recovery, while at the same time lessening, or inhibiting, the maladaptive processes that lead to secondary, progressive tissue damage and cell death.

While the bases for any possible synergistic advantages of the present formulations have been heretofore unknown, as have been the present combinations, the formulations are directed toward modifying both adaptive and maladaptive processes. Embodiments of the invention are directed with the proposition that neurological outcomes that are known to result from trauma can be reduced or prevented, or the risk of such outcomes can be reduced or prevented, by the administration of a formulation of compounds that combine neurotrophic actions to repair and restore, as well as neuroprotective actions to prevent or reduce the incidence and severity of secondary injury or damage that results from trauma.

7. Compound Groups of the Formulations

While not intending to be bound by any one theory or set of theories, in one underlying aspect, applicant speculates that the formulations of the invention possess unexpected advantages in part because they do not rely on affecting just one neurological mechanism. Instead, Applicant believes that the present formulations are adapted and arranged to affect several adaptive, as well as several maladaptive, underlying mechanisms. Alternatively stated, some of the components of the present formulations are selected to maximize the recovery processes initiated by the trauma, while other components are selected to minimize or prevent the destructive processes initiated by that same trauma. In doing so, formulations of the invention are believed to achieve complementary positive effects that would not be achieved by formulations that affect only one of the involved mechanisms. Moreover, Applicant speculates that the specific formulations disclosed herein are especially effective when compared to other multiple-drug approaches.

Anticonvulsant drugs, or antiepileptic drugs, are used, as the name indicates, to treat epilepsy. However, they are also used extensively off-label. For example, the broadest off-label use of gabapentin is to treat neuropathic pain. While anticonvulsant drugs are recommended as treatment of the outcomes of neuropathy they appear to not be used for prevention of neuropathy or protection from secondary injury that results from trauma of any type. Gabapentin is included in this invention to inhibit reported maladaptive processes that trigger and are involved in pathophysiological changes in nerve cells, in neural support cells and in neural support tissues, particularly endothelial cells, that result from trauma of any type. There is a wide range of downstream mechanisms that are inhibited by gabapentin, such as reducing or preventing calcium influx into cells and calcium release from intracellular stores that trigger activation of calcium-dependent catalytic enzymes, and other processes. Gabapentin has been shown to have preventive effects in human studies. For example, a recent systematic review and meta-analysis concludes that there is sufficient evidence of beneficial effects of perioperative administration of gabapentin in reducing the incidence of chronic post-surgical pain at two months or more after various types of surgery, including arthroplasty, thyroid surgery, breast surgery, cardiac surgery, hysterectomy surgery, inguinal herniorrhaphy and caesarian delivery. Lapolla et al. (Incidence of postherpetic neuralgia after combination treatment with gabapentin and valacyclovir in patients with acute herpes zoster: open-label study. Arch Dermatol 147: 901-907, 2011) have reported that when gabapentin is combined with valacyclovir in patients with acute herpes zoster the rate of postherpetic neuralgia at six months later is reduced. Thus, while it had acute effects, when administered during a phase when the processes leading to neuropathic pain were developing, gabapentin was effective in reducing or preventing the late-developing adverse health conditions.

Animal studies have also provided evidence for preventive effects of gabapentin on outcomes of neuropathology. This includes animal models of spinal cord ischemia (Kale et al., Neuroprotective effects of gabapentin on models of spinal cord ischemia-reperfusion injury in rabbits. J Neurosurg Spine 15: 228-237, 2011) and spinal cord compression (Emmez et al., Neuroprotective effects of gabapentin in experimental spinal cord injury. World Neurosurg 73: 7290734, 2010). Treatment of acute seizures with gabapentin in a mouse model has also been shown to have beneficial effects on brain atrophy when measured even four weeks later (Traa et al., Gabapentin neuroprotection and seizure suppression in immature mouse brain ischemia. Pediatr Res. 64: 81-85, 2008).

Neurosteroids, which are also called neuroactive steroids, include progesterone, pregnenolone, allopregnanolone and dehydroepiandrosterone and many others, and include their metabolites and their sulfates and other derivatives. Neurosteroids are generally thought of as peripherally-acting steroids but they are also synthesized by nerve cells and glial cells in the central nervous system. Neurosteroid receptors are also synthesized by nerve cells and support cells in the central nervous system and in the periphery. Enzymes are present in such neural tissue for the breakdown of neurosteroids to other metabolites.

Progesterone is thought to act through a number of different mechanisms. For example, progesterone acts on progesterone receptors that are distributed throughout the central and peripheral nervous systems. Progesterone may also act through a diverse number of other mechanisms to protect neurons and glial cells from secondary injury, including acting on intracellular receptors, membrane ion channels and allosteric sites on membrane-bound receptors.

Applicant has found that early administration of progesterone given intraperitoneally prevents the development of symptoms of peripheral nerve injury (Dableh and Henry, Progesterone prevents development of a rat model of neuropathic pain: timing and duration of treatment are critical. J Pain Research 4: 91-101, 2011). An animal model of peripheral neuropathy was used, in which a thin polyethylene cuff is inserted around the sciatic nerve. This typically induces a tactile hypersensitivity in the respective hind paw that begins to develop within 24 hours, reaches a maximum at five to seven days, and persists. When progesterone was given starting one hour after model induction, and was given daily for the subsequent 10 days tactile hypersensitivity developed over the first 20 days similar to that in a control group given vehicle only. However, by 30 days the two groups were different, and the treatment group exhibited no tactile hypersensitivity. Even though the progesterone treatment ended on day 10 this effect of progesterone persisted to the end of the study period, which ended at day 85. Importantly, in another group, in which progesterone was given for 11 days, starting on day 20, there was no difference between this experimental group and the control group. This suggests that early treatment but not later treatment is effective in preventing development of the hypersensitivity.

Neurosteroids and related hormone therapy have been proposed to have positive outcomes in human clinical trials for traumatic brain injury (Stein and Wright, Progesterone in the clinical treatment of acute traumatic brain injury. Expert Opin Investig Drugs. 19: 847-857, 2010), central nervous system ischemia (Gibson et al, Is progesterone a candidate neuroprotective factor for treatment following ischemic stroke? Neuroscientist. 2009 August; 15(4):324-332, 2009), spinal cord injury (Popovic et al., A reassessment of a classic neuroprotective combination therapy for spinal cord injured rats: LPS/pregnenolone/indomethacin. Exp Neurol. 233:677-685, 2011) and peripheral nerve injury (Roglio et al., Docetaxel-induced peripheral neuropathy: protective effects of dihydroprogesterone and progesterone in an experimental model. J Peripher Nerv Syst. 14: 36-44, 2009). Xiao et al. (Improved outcomes from the administration of progesterone for patients with acute severe traumatic brain injury: a randomized controlled trial. Crit. Care. 12: R61, 2008) have reported improved neurological outcomes in a prospective, randomized, placebo-controlled phase III clinical trial in approximately 80 patients who were treated within eight hours after traumatic brain injury. An NIH-sponsored trial is apparently on-going at present (Wright et al., ProTECT: a randomized clinical trial of progesterone for acute traumatic brain injury. Ann Emerg Med 49:391-402, 2007). With the exception of combination therapy with vitamin D (Cekic et al., Combination treatment with progesterone and vitamin D hormone may be more effective than monotherapy for nervous system injury and disease. Front Neuroendocrinol. 30: 158-172, 2009) what has not appeared to be considered strongly is the improved benefit of combination of a neurosteroid with other neurotrophic, neuroprotective or neuron-sparing therapeutics.

Applicant has found that administration of an NK-1 receptor antagonist, CP-96,345, promotes the recovery from peripheral nerve injury in an animal model (Dableh et al., 2011). In the rat model of peripheral nerve injury described herein, at the first reading of nociceptive scores, measured as withdrawal threshold from calibrated von Frey filaments, cuff-implanted rats demonstrated tactile hypersensitivity, the animal parallel to allodynia in humans. This effect became maximum at day three and persisted throughout the testing period, which ended 42 days after model induction. A physiological reversal of this tactile hypersensitivity was demonstrated in another group of rats by removing the cuff after 24 hours, and monitoring withdrawal threshold until 42 days after model induction. In this case, the tactile hypersensitivity developed only partially, and by day 18 it had reversed completely. In contrast, in a third group, when the cuff was removed on the fourth day recovery was delayed until day 25, and full recovery was never attained. This partial recovery indicated that between 24 hours and four days processes occur that result in prolonged, perhaps permanent, changes in nociceptive mechanisms, leading to tactile hypersensitivity.

NK-1 receptor antagonists have been the focus of intense research effort since the introduction of the first non-peptide antagonist CP-96,345 and its demonstrated biological effectiveness in vivo (Radhakrishnan and Henry, Novel substance P antagonist, CP-96,345, blocks responses of cat spinal dorsal horn neurons to noxious cutaneous stimulation and to substance P. Neurosci. Lett. 132: 39-43, 1991). To date, over 300 patents have been filed for over 25 new chemical entities targeting this receptor. In animal studies, among the reported beneficial outcomes of administration of NK-1 antagonists is neuroprotection. For example, in a recent review of the actions of substance P and potential therapeutic benefit of administration of NK-1 antagonists, Thornton et al. (Kinin receptor antagonists as potential neuroprotective agents in central nervous system injury. Molecules. 15:6598-6618, 2010) stress the potential benefit of these antagonists in prevention of secondary injury arising from traumatic brain injury, spinal cord injury and ischemic stroke. This extensive review did not, however, distinguish treatment of established symptoms or disorders from intervention to reduce or prevent secondary injury resulting from trauma. One could consider pre-emptive administration of the NK-1 receptor antagonist, aprepitant (Emend, Ivermend), as a preventive measure, but this administration was for acute effects on chemotherapy-induced nausea and vomiting, upon which the antagonist proved to be effective when administered in conjunction with another antiemetic drug. Aprepitant was not tested for effects on chemotherapy-induced cell death or on neuropathology or processes that lead to loss of function of nerve cells, neural support cells or neural support tissues.

Endpoints for treatment with aprepitant target mainly acute nausea and vomiting induced by chemotherapy. A few clinical trials have been run targeting acute treatment of tinnitus, insomnia, depression, anxiety and post-traumatic stress disorder, but these trials have not culminated in positive outcomes (Mathew et al., A selective neurokinin-1 receptor antagonist in chronic PTSD: a randomized, double-blind, placebo-controlled proof-of-concept trial. Eur Neuropsychopharmacol. 21:221-229, 2011; Ratti et al., Results from 2 randomized, double-blind, placebo-controlled studies of the novel NK1 receptor antagonist casopitant in patients with major depressive disorder. J Clin Psychopharmacol. 31:727-733, 2011). In particular, despite stellar effects on acute nociception in animal models, clinical trials on NK-1 receptor antagonists have failed to demonstrate effectiveness in acute treatment of chronic pain in humans (Goldstein et al., Dose-response study of the analgesic effect of lanepitant in patients with painful diabetic neuropathy. Clin Neuropharmacol 24:16-22, 2001; Diener, RPR100893, a substance-P antagonist, is not effective in the treatment of migraine attacks. Cephalalgia 23: 183-185, 2003). A review of the literature did not find reports where long term outcomes with aprepitant treatment were studied.

As another example, fosaprepitant, an NK-1 receptor antagonist that is the prodrug of aprepitant, is typically administered intravenously. Current clinical literature recommends a bolus ranging from 115 to 150 mg of fosaprepitant, at a concentration of 1 mg/ml, followed by aprepitant orally on days two and three of a three-day regimen, for chemotherapy-induced nausea and vomiting.

Lithium has been reported to have both neurotrophic actions to promote cellular health and function as well as neuroprotective actions to inhibit apoptosis and cell death. Adaptive processes promoted by lithium include upregulation of anti-apoptotic pathways including those involving Bcl-2 and the cytoprotective protein, heat shock protein 60, as well as activation of the P13K/Akt cell survival pathway. Maladaptive processes that are inhibited by lithium include downregulation of apoptotic proteins, downregulation of the pro-apoptotic p42 pathway and inhibition of microglia activation, depletion of inositol that otherwise inhibits growth cones in cultured sensory neurons, as well as inhibition of phosphatases that interfere with the function of cell surface G protein-coupled receptors. Lithium is best known as a mood stabilizer, prescribed for over 60 years for bipolar disorder, and to a lesser extent for depression, although the specific mechanisms by which mood is stabilized remain unclear.

In terms of promotion of adaptive changes, one principal action of lithium-related drugs is inhibition of glycogen synthase kinase-3β, an enzyme that inhibits axon growth cone development and proliferation. Thus, one action of lithium-related drugs is to disinhibit a restorative process following trauma.

Another principal action of lithium-related drugs is induction of cellular signaling by brain-derived neurotrophic factor (BDNF), which promotes pathways involved in cell survival, as well as upregulation of the BDNF receptor, tyrosine receptor kinase B. BDNF has a number of actions, including stimulation of cell-surface trophic factor receptors such as tyrosine receptor kinase B (TrkB), the receptor of brain-derived neurotrophic factor, insulin, and other growth factors. BDNF also activates multiple survival pathways including the phosphoinositide 3-kinases (PI3K)/Akt pathway and the MAP kinase (MEK)/extracellular-signal regulated kinase (ERK) pathway. BDNF increases progenitor cell proliferation in brain and spinal cord following ischemia.

A third principal action of lithium is inhibition of calcium influx into neurons via the N-methyl-D-aspartate glutamate receptor. This action results from the attenuation of constitutive phosphorylation at Tyr1472 of the NR2B subunit of the NMDA receptor, which is catalyzed by Fyn, a member of the Src tyrosine kinase family. Neither total tyrosine protein kinase activity nor that of tyrosine protein phosphatase is affected by this drug, indicating the selectivity of the modulation of the NMDA receptor and its contribution to neuroprotection. Thus, a third principal action of lithium-related drugs is to protect against calcium-dependent intracellular mechanisms that lead to loss of cell function or to cell death.

A phase I clinical trial examining the safety and pharmacokinetics in chronic spinal cord injury patients indicated that lithium carbonate is well tolerated over the first two weeks and that individual titration is essential to maintain optimal serum levels within the therapeutic range. Yet in a phase II clinical trial lithium carbonate was found to be without effect on neurological symptoms in spinal cord injury patients. With regard to the presently disclosed invention embodiments, it is relevant that this phase II clinical trial was run only on patients with stable chronic spinal cord injury. It was not tested on patients immediately after, or even within days of spinal injury, and thus it is not known whether there could be beneficial effects of lithium carbonate administration on protecting against secondary nerve injury following spinal cord trauma. In a clinical study on patients with amyotrophic lateral sclerosis daily doses of oral lithium carbonate leading to 0.4-0.8 mmol/L plasma levels prevented death of 22 patients yet resulted in only minimal motor deterioration over 15 months, compared to a 29% mortality and significant motor deterioration in 22 patients that did not receive lithium. Thus, whether amyotrophic lateral sclerosis is considered to be due to a gene mutation, to excessive glutamate or an autoimmune disease, it is nonetheless a result of motor neuron cell death in the spinal cord and this beneficial effect of lithium treatment may reflect a broader neuron sparing effect.

In two peripheral nerve crush injury models in the mouse, a facial nerve injury model and a sciatic nerve injury model, lithium chloride was found to stimulate the expression of myelin genes, restore myelin structure and accelerate functional recovery; this effect was attributed to β-catenin binding to R-cell factor/lymphoid-enhancer factor response element identified in myelin genes. In a rat partial sciatic nerve ligation model lithium chloride administration reduced the nociceptive scores in response to tactile and thermal stimuli compared to controls.

8. The Contributions Made by the Invention

The present invention provides heretofore unknown advantages in the treatment and prevention and reduction of trauma-induced damage and injury to nerve cells or neural support cells or neural support tissues. The presently disclosed technology and its embodiments aim to fill a gap in standard practice for treating victims of trauma. This is the gap, as described herein, that exists between standard emergency practice and standard rehabilitation practice. This gap represents an unsolved medical need. The presently disclosed technology aims to fill this gap.

The presently disclosed technology focuses on reducing the negative consequences that can and frequently do follow or ensue from trauma. In the context of invention embodiments, a traumatic event causes a primary injury to tissues including nerve cells, neural support cells or neural support tissues. Cell loss caused by this primary injury is beyond treatment. However, the injury to neural tissues in the area of this primary injury spreads through secondary injury mechanisms in time as well as to neighboring and even remote cells and tissues, including nerve cells, neural support cells and neural support tissues, that do not die from this primary injury. Indeed, the damage caused by these secondary processes can be as serious and extensive as, or even more serious and extensive than, that caused by the primary trauma. Secondary processes also progress over time so that injury and damage can continue over the days, weeks and even months after the initial injury. Further, the secondary processes can also progress spatially so that injury and damage can spread to other parts of the body and manifest at sites remote from the site of the primary trauma, whether in the brain, brainstem, spinal cord, enteric nervous system or peripheral nervous system.

This balance can be tipped toward normal function and health by appropriate pharmaceutical intervention at the appropriate time. This can be achieved because of the chemical nature or basis of the adaptive and maladaptive processes occurring at the cellular, biochemical and metabolic levels.

Adaptive mechanisms: as detailed herein there are many targets or points of entry for pharmaceutical promotion, facilitation or potentiation of adaptive processes to tip this balance toward function and health, in order to reduce or prevent the loss of function, the adverse health conditions or the disability that can and often do result from a traumatic event. The presently disclosed technology and its embodiments are based on a select few targets or points of entry, as represented in the formulations of the presently disclosed technology. This selection of specific, synergistic compounds of the formulations is based on fundamental and clinical evidence detailed herein and elsewhere that is available and understood by a person having ordinary skill in the art.

Maladaptive mechanisms: as detailed herein there are many targets or points of entry for pharmaceutical inhibition, lessening or blocking the maladaptive processes that tip this balance away from function and health toward loss of function, adverse health conditions or disability. Such an approach is taken in order to reduce or prevent the loss of function, the adverse health conditions or the disability that can and often do result from a traumatic event. The presently disclosed technology and its embodiments are based on a select few targets or points of entry to reduce the maladaptive processes, as represented in the formulations of the presently disclosed technology. This selection of specific, synergistic compounds of the formulations is based on fundamental and clinical evidence detailed herein and elsewhere that is available and understood by a person having ordinary skill in the art.

Conventional or standard immediate or emergency treatment of trauma typically consists of minimizing the symptoms of the immediate, or primary, traumatic injury. In significant contrast, the primary aspect of the presently disclosed technology does not focus on either reducing the immediate trauma or rehabilitating long-term disability once this disability has been established. Instead, embodiments of the invention are directed toward the sequalae of post-trauma effects that are an indirect result of the primary trauma. The aim is to incorporate the presently disclosed technology into standard emergency health care, as well as to practice the presently disclosed invention as standard preventive and prophylactic practice.

Significantly, a point of differentiation between conventional or standard methods and the presently disclosed technology is the difference between the treatment of the symptoms of the primary injury, and formulations, methods and procedures taken at or about the time of trauma to prevent or lessen damage from the secondary sequalae that, without the benefit of the presently disclosed technology, may or are likely to occur. Thus, an important aspect of the presently disclosed technology is its usefulness in treating to prevent injuries that are expected or likely to occur, but that are not the damage caused immediately and directly by a traumatic event. Alternatively stated, the presently disclosed technology is distinguished by its prevention or amelioration of the secondary sequalae versus the treatment of the primary injury.

Secondary injury spreads to sites remote from the primary injury. In fact, the cascades of mechanisms leading to secondary injury at remote sites are also triggered locally at the site of the primary injury. The presently disclosed technology aims to reduce or prevent this secondary injury irrespective of whether this manifests locally or more remotely.

Conventional rehabilitation treatment is aimed at ameliorating existing symptoms, adverse health conditions or disability caused by the primary injury. These typical existing symptoms are easily recognized and can be measured. In significant contrast is the presently disclosed technology, where prevention is aimed at symptoms that are neither existent nor present at the time immediately following a traumatic event, but which have a likelihood to manifest if not reduced or prevented based on knowledge of their incidence with respect to the category of primary injury.

As indicated herein, the cascades of mechanisms leading to secondary injury are triggered within minutes and hours, yet continue to occur over the ensuing days, weeks and months. As a result, symptoms of secondary injury manifest over such periods, and the presently disclosed technology aims to reduce or prevent the manifestation or expression of these symptoms of secondary injury, which are known on the basis of incidence studies to occur. As a result, the presently disclosed technology addresses symptoms that are non-apparent, but that can be expected to occur with a known incidence if not reduced or prevented by appropriate pharmaceutical intervention.

Despite this, it is known with certainty that trauma activates secondary injury mechanisms in a significant percentage of victims or patients. What can be measured with respect to these secondary injuries, then, is the incidence, measured at later time points after a category of traumatic events, by comparisons that can be made. Such comparisons are made, as examples, of the number of people who, after a category of traumatic events, show symptoms that typically manifest long term in individuals that have been treated by standard procedures alone, with the number of people showing symptoms that are observed in individuals that have been treated by standard procedures along with the administration of formulations of the presently disclosed technology in accordance with embodiments of the presently disclosed technology.

Similarly, comparisons can be made of the severity of the symptoms that typically manifest after a category of traumatic event in those individuals that have been treated with standard procedures alone, with the severity of symptoms in those treated with standard procedures along with the practice of invention embodiments, including administration of formulations of the presently disclosed technology and the methods and procedures as described herein.

(i) The presently disclosed technology and its particular embodiments provide numerous formulations that comprise combinations of complementary existing chemical entities that have not been combined as in the presently disclosed technology. In one aspect, the specific chemical entities included in formulations of invention embodiments are selected along informed and rationalized lines of thought derived from an understanding of the intrinsic mechanisms that are triggered by primary injury and an understanding of the mechanisms of the secondary sequalae of this primary injury.

(ii) The biological targets of embodiments of formulations provided herein include mechanisms of the secondary sequalae that are adaptive and function to restore neurons, neural support cells and neural support tissues toward their condition before the trauma and as well include mechanisms of the secondary sequalae that are maladaptive processes, which drive neurons, neural support cells and neural support tissues toward pathology, or loss of function or even cell death. Formulations of invention embodiments are therefore advantageous for the provided combination of specific chemical entities that, combined, reduce or prevent, or reduce the risk of, secondary damage indirectly resulting from, or triggered by, the trauma event.

(iii) The present disclosure provides new uses of each of the chemical entities in the formulations of invention embodiments. Evidence is cited in the description of the invention supporting the current uses of each of the families of chemical entity that are included in the formulation. There is some evidence that certain members of each of the four classes of chemical entity may have some neuron-sparing effect, but to date these have not been used to reduce or prevent, or reduce the risk, of secondary injury to nerve cells, to neural support cells and neural support tissues and to endothelial cells resulting from trauma.

(iv) The formulations are advantageous also in that they are directed at maximizing, potentiating or facilitating naturally-occurring adaptive mechanisms, while at the same time minimizing, reducing or inhibiting naturally-occurring maladaptive processes. There is currently no medical intervention that purposefully targets both adaptive and maladaptive processes that are triggered by trauma and that govern, recover from or lead to secondary injury to nerve cells, neural support cells and neural support tissues or endothelial cells.

(v) The presently disclosed technology is advantageous in that the formulations target trauma-induced secondary injury to nerve cells. Further, the presently disclosed technology also targets trauma-induced secondary injury to neural support cells and neural support tissues. Even further, the presently disclosed technology also targets trauma-induced secondary injury to endothelial cells. As loss of function of neural support cells and neural support tissues and endothelial cells can contribute to overall secondary injury to nerve cells, protection of injury to neural support cells and neural support tissues and endothelial cells is also included in the presently disclosed technology.

(vi) The presently disclosed technology is advantageous in that it targets secondary injury to nerve cells, to neural support cells and neural support tissues, and to endothelial cells resulting from physical, chemical, metabolic, medical, surgical or other trauma. The presently disclosed technology outlines the various forms that each of these types of trauma manifests and the presently disclosed technology describes how the formulations, methods and procedures of the presently disclosed technology will prevent or reduce, or reduce the risk of, secondary injury to nerve cells, to neural support cells and neural support tissues, and to endothelial cells, that results from traumatic brain injury, ischemia of the central nervous system, spinal cord injury, enteric nervous system injury or peripheral nerve injury. It is the intent of the presently disclosed technology to include the full spectrum of trauma and traumatic events that lead to secondary injury to nerve cells, to neural support cells and neural support tissues, and to endothelial cells inclusive of all parts of the body.

(vii) There is evidence from animal studies that early intervention at the time of trauma reduces the incidence as well as the severity of long term functional deficits. In one important aspect, the presently disclosed technology is advantageous in that it directs specific formulations to administration to humans.

(viii) The presently disclosed technology is advantageous in that a formulation is to be given beginning at specific times before, at the time of or immediately following trauma and continued as needed.

(ix) The presently disclosed technology is advantageous in that it specifies that a formulation is to be given differently depending on the setting, which is described for purposes of illustration but not limitation, as the home setting, the prehospital setting, or any setting outside the home and outside a hospital or sufficiently equipped clinical setting, where premedic or medic intervention is possible, and a hospital or clinical setting that is fully staffed and equipped for the full range of healthcare.

(x) The presently disclosed technology is advantageous in that it specifies the timing of administration of the formulation, depending upon the specific setting, as referred to in herein.

(xi) The presently disclosed technology is advantageous in that the route of administration is dependent upon the specific setting, as defined herein and as in examples of the particular embodiments.

(xii) The presently disclosed technology is advantageous in that the formulations are applied differentially for unanticipated vs. anticipated trauma. Medical interventions or procedures, including those described herein, can lead to neuropathology. With respect to anticipated trauma, the presently disclosed technology is directed to reduce the known incidence of neuropathology as outlined herein, and thereby reduce the known long term disability and loss of function that result from the medical interventions described herein. The presently disclosed technology is advantageous in reducing or preventing, or reducing the risk, of injury to nerve cells, neural support cells and neural support tissues, and endothelial cells that occurs or can occur as a result of surgical or other medical interventions or procedures.

All types of trauma, including those addressed in the presently disclosed technology extract a heavy toll on individuals, on families, on the health care system and on the economy. These types of trauma include, as examples but are not limited to, traumatic brain injury, central nervous system ischemia, spinal cord injury, enteric nervous system injury and peripheral nerve injury. Primary injuries resulting from these types of trauma are not amenable to prevention or reduction, but the secondary processes triggered by the primary trauma are, with the benefit of invention embodiments, amenable to medical intervention.

9. References Material to the Field and Background of the Invention

References in the relevant art simply neither comprehend nor teach the synergistic compositions of the formulations of the presently disclosed technology. Before the present invention, there have been no combination pharmaceutical formulations to reduce or prevent the secondary injury that results from trauma. The presently disclosed technology is a combination of pharmaceutical compounds. Those combinations have heretofore unknown synergistic effects. Applicant theorizes that the effectiveness of the present formulations is at least partially due to the heretofore unknown synergistic actions of drug compounds directed at multiple targets, including promoting multiple targets that function to restore or rescue cells from damage, as well as inhibiting multiple targets that function to drive cells toward loss of function and cell death.

Regarding of the underlying physiological and neurological mechanisms, until the presently disclosed formulations and methods, no effective combinations of compounds from the four groups herein have been known. Further, combinations of these compounds of two, three or all four have not been used in reducing or preventing secondary injury and its sequalae resulting from trauma. Therefore, the presently disclosed technology is advantageous in providing synergistic therapeutic formulations for preventing or reducing neuropathology that results from trauma.

10. Practice Embodiments of the Invention

The formulations, methods, procedures and systems of the presently disclosed technology provide a significant number of combinations of formulations, formulation components, dosages, administration sequences, patterns and combinations thereof to offer efficacious and safe anticipatory (pretrauma) and posttrauma treatments for secondary damage or injury to nerve cells, neural support cells or neural support tissues.

To illustrate some of these permutations, Applicant presents herein some examples of the many particular embodiments of the invention, while noting that a person having ordinary skill in the art, armed with the present disclosure, would be able to comprehend and practice numerous forms of the formulations, methods, procedures and systems of invention embodiments, while adapting them to specific uses and circumstances and can do so without undue experimentation.

By way of scientific background, and as further described herein, all nerve cells, neural support cells and neural support tissues undergo similar changes as a result of trauma, irrespective of whether these neurons are in the brain, the brainstem, the cerebellum, the spinal cord, or in the enteric nervous system or the periphery. The terminology "trauma" is broadly interpreted as explicated in its definitions and delineations as described herein.

The same or similar adaptive and maladaptive processes, as defined herein, are triggered in nerve cells, neural support cells or neural support tissues, by trauma, irrespective of the site or the type of neuron or cell. While there may be some minor differences, such as the difference in sensitivity to excitotoxicity of neurons in the hippocampus vs. neurons in the cerebral cortex, the physiological processes triggered by trauma are believed to be the same, or quite similar, in all neurons.

These physiological processes, including both the adaptive and the maladaptive processes, are activated within seconds or minutes by a traumatic event, and continue to develop over the minutes, hours, days and even months following the trauma. Each change that is activated or triggered by trauma sets off a process or cascade of biochemical and metabolic changes, as detailed herein. As a person having ordinary skill in the art will understand, as a result of the activation of maladaptive processes, it is advised that treatment be initiated at the earliest possible time in order to arrest or prevent further changes along the cascade. Similarly, it is advised that the adaptive processes or cascades be facilitated or promoted to counteract the maladaptive cascades and processes, and before irreparable damage can be done to the nerve cells, neural support cells or neural support tissues. The view of the Applicant is that there is a platinum hour, a golden day and a silver week within which optimal protection from trauma and neuropathology can be achieved, especially in the contexts of the presently disclosed technology and its embodiments. If allowed to progress, much of the neuropathology is entrenched and cannot be prevented or reversed, leading to permanent adverse health conditions or disability.

Whether the invention embodiments are practiced with respect to traumatic brain injury, central nervous system ischemia, spinal cord injury, enteric nervous system injury or peripheral nerve injury practice of the invention, as indicated herein with examples of particular embodiments, occurs within the same or similar treatment parameters. As detailed herein, a key aspect of the invention in some particular embodiments relates to the timing of the administration of one or more of the present formulations. In accordance with this aspect, the timing of the administration of formulations of the invention is preferably adapted and arranged with respect to the traumatic event itself. Thus, the practice of the invention can be before a traumatic event has occurred or after a traumatic event has occurred. This timing aspect can be described generally with respect to three situations in which many embodiments of the invention are to be practiced: A) precautionary administration, B) prophylactic administration and C) posttraumatic event administration. Specific examples are provided herein to illustrate these three types of practice of invention embodiments, but are presented as examples only and do not exclude other practices of the invention.

Precautionary practice of invention embodiments includes, situations where an individual is about to enter into a high-risk situation or condition where trauma may occur. Precautionary practice would be an exigent practice, exigent circumstance practice, or contingency practice and is different from prophylactic practice or posttraumatic event practice.

Embodiments of the invention are useful also in circumstances where a trauma is quite likely to occur, or whenever it is even anticipated. Embodiments of the invention that are precautionary in nature are quite useful, and fill a void which presently exists with respect to the treatment or prevention of trauma-induced neuropathology in high risk conditions or situations.

In such cases of great likelihood of trauma being soon endured by one or more individuals, the presently disclosed technology is uniquely applicable. In such cases, no traumatic event has yet occurred at the time that a formulation of invention embodiments is taken by a subject or administered to a subject. In such precautionary embodiments of the methods, procedures, means and systems of embodiments of the invention, a formulation is administered before the highly expected trauma event or at the time of the pre-trauma awareness that a potential trauma exists.

In some embodiments lithium is not included in the usual four-component formulation because of its relatively narrow therapeutic dose range and the relatively low threshold for adverse effects. In other words, lithium is not included unless there is an actual traumatic event, in which case practice of the invention will follow the formulations methods and procedures represented herein as posttraumatic event practice embodiments Prophylactic practice of invention embodiments includes situations where a procedure, particularly a medical procedure, is about to take place wherein the procedure is known to produce, or where evidence suggests it may produce, trauma, damage or injury to nerve cells or neural support cells or neural support tissues in some patients, whether in the central nervous system, the peripheral nervous system or the enteric nervous system. Prophylactic practice is thus distinguishable from precautionary practice or posttraumatic event practice.

Embodiments of the invention are useful in medical circumstances where evidence from clinical studies indicates that damage to nerves or nerve cells, or neural support cells or neural support tissues may result from a medical procedure, such as surgery or other medical treatment or medical procedure, for example but not exclusive to chemotherapy or radiation therapy. Embodiments of the invention that are prophylactic in nature are quite useful, and fill a void which presently exists with respect to the prevention of neuropathology that may result from surgery or medical treatment of medical procedure. Embodiments of the invention include types of situations or scenarios where there is known or substantiated evidence that neuropathology, or damage to nerve cells, or neural support cells or neural support tissues may be or will be an outcome of surgery or other medical treatment or medical procedure in some patients.

Posttraumatic event practice of invention embodiments includes any situation or condition where a traumatic event is occurring or has occurred, and there is known, or there is reason to suspect, damage, injury or cell death to nerve cells, neural support cells and neural support tissues, whether in the central nervous system, the peripheral nervous system or the enteric nervous system. Posttraumatic practice is thus distinguished from precautionary practice or prophylactic practice.

Embodiments of the invention are useful in circumstances where a traumatic event has taken place and there is trauma or suspected trauma to the central nervous system, the peripheral nervous system or the enteric nervous system, comprising any neuron, set of neurons, nerve or nerve cell, or any cell or tissue that supports the health or survival of nerve cells directly or indirectly.

Embodiments of the invention that are posttraumatic in nature are quite useful, and fill a void which presently exists with respect to the treatment or prevention of neuropathology, or the risk of neuropathology that may result from a traumatic event.

In such posttraumatic embodiments of the methods, procedures, means and systems of embodiments of the invention, the formulation is administered as soon as possible after the traumatic event has occurred. In cases of an on-going or continuing traumatic event, the formulation is administered during the traumatic event or as soon afterward as possible. Administration of the formulation is continued as needed.

11. Therapeutic Advantages Particularly Associated with the Disclosed Multi-Agent Formulations Applicant anticipates that multi-agent formulations, as disclosed herein, will provide substantial therapeutic advantages over existing therapeutic formulations related to the agents included in such formulations, which, so far as applicant is aware, are single active agent formulations. Applicant anticipates that the coincident therapeutic use of multiple agents as disclosed herein, with separate mechanisms of action, will provide therapeutic benefits for particular neurological conditions, as disclosed herein, that substantially exceed the benefits that could be ascribed to the use of any agent alone. With reference to therapeutic benefits in excess of those that could be derived from any single agent, alone, the enhancement due to combination therapy could be additive or it could be synergistic. By additive, it is meant that the total benefit of a multi-agent formulation exceeds that which could be maximally achieved by any single agent as a monotherapy, regardless of the maximal effective dose of any single agent. By synergistic, it is meant that the total benefit of a multi-agent formulation exceeds even that which might be expected from adding the maximal therapeutic benefits from each of the agents as a monotherapy.

Applicant further anticipates that the dosage-response profiles of individual agents, when administered in multi-agent formulations as provided herein, and for the conditions as described herein, may be left-shifted. By left-shifted, it is meant that that maximal effective dosages of individual agents in multi-agent formulations may be lower than dosages required for maximal therapeutic effect when the individual agents as used as a monotherapy. The use of lower dosages of the individual agents may advantageous in terms of minimizing unwanted side effects of the agents that are associated with high dosages of the agent, particularly when used as a monotherapy. Lower dosages also provide a clear economic advantage to such multi-agent formulations.

Another aspect of therapeutic or safety advantages of the presently disclosed multi-agent formulations relates to minimizing the possibility of abusive uses of individual agents. Some anti-convulsants, such as barbiturates and benzodiazepines, have a burden of being used as drugs of abuse or recreational use. In practical terms, including drugs of potential abuse within a multi-agent formulation tends to discourage its recreational or abusive use.

Coformulation of multiple agents, as provided herein offers still further therapeutic advantages over monotherapy in that sequential and timed release strategies may be usefully applied to individual agents within the multi-agent formulation. The many uses and advantages of sequential or timed-release formulations are discussed elsewhere in this disclosure. For example, it may be advantageous to stage the pharmacodynamics of agents, as disclosed herein, independently of each other. By way of particular example, it may be advantageous for the circulatory profiles of individual agents to be temporally staged with respect to each other (one agent having a circulatory profile that precedes the profile of a second agent). Such level of therapeutic choreography is significantly more controllable in multi-agent formulations delivered as a single pill, rather than multiple monotherapeutic formulations being delivered in separate pills.

12. Dose Ranges of Constituents of Formulations Representing Particular Embodiments of the Invention certainty that specific dosages, or specific dosage ranges, can be determined with respect to many other combinations and permutations with the assistance of the present Specification and procedures known in the art which can be adapted without undue experimentation.

DETAILED DESCRIPTION OF THE INVENTION

It is therefore an object of the invention to provide formulations adapted and arranged for accomplishing one or more of preventing, ameliorating, lessening or eliminating the damages incident to many kinds and types of trauma to mammals, and especially to human beings.

It is another object of the invention to provide means and methods for administering formulations of the invention to accomplish these same goals and effects.

It is also an object of the invention to provide methods and means combined with formulations to be administered with respect to the time of the trauma, including beforehand, during, immediately afterward, and in a sustained manner for hours, days, weeks or months thereafter.

In accordance with these and other objects, formulations of the invention are adapted and provided for the prevention of the development of neuropathology, and for the amelioration of the effects caused by trauma to a subject, the formulation comprising four biologically active compounds. Preferably, the four biologically active compounds are provided in amounts that are pharmaceutically effective for each compound, respectively, when administered in combination with the other three biologically active compounds. In some preferred embodiments of the invention, the four compounds comprise a pharmaceutically effective amount of A) at least one biologically active compound selected from the group comprising anticonvulsants, wherein the anticonvulsant is at least one form of one or more of gabapentin, pregabalin, and valproic acid; B) at least one biologically active compound from the group comprising neurosteroids, wherein the neurosteroidal agent is at least one form of one or more selected from the group comprising progesterone, methylprednisolone, and medroxyprogesterone acetate; C) at least one biologically active compound from the group comprising NK-1 receptor antagonists, wherein the NK-1 receptor antagonist is at least one form of one or more selected from the group comprising aprepitant, vestipitant, and casopitant; and D) at least one biologically active compound from the group comprising lithium-containing compounds, wherein the lithium-containing compound is at least one form of one or more of lithium carbonate, lithium citrate and lithium chloride.

Advantageously, the formulations of the invention are provided in a form and a dosage with respect to each of the formulations' components or compounds such that a formulation of the invention is adapted and arranged for adminis-

TABLE 1

| Compound | Acceptable Range (mg) | Preferable Range (mg) | More Preferable Range (mg) | Most Preferable Range (mg) |
|---|---|---|---|---|
| Gabapentin | 5-9,600 | 50-4,800 | 100-2,400 | 200-600 |
| Progesterone | 0.05-1,200 | 5-600 | 50-450 | 100-300 |
| Aprepitant | 0.05-750 | 5-375 | 20-250 | 40-120 |
| Lithium Carbonate | 0.5-3,600 | 30-1,800 | 100-900 | 200-600 |

Dose ranges for constituents of formulations are based to some extent on ranges of standard practice and are intended as exemplary, and not limiting. Instead, they are provided as additional guidance with respect to the invention embodiments, although those of skill in the art will comprehend with tration to a mammal in need thereof, such as a human, so that the development, or the risk of development, of neuropathology is reduced, lessened, attenuated or prevented. The formulations and methods of the invention are particularly useful in the treatment of human beings.

Numerous combinations, variations and permutations of preferred formulations of the invention can be provided while remaining within the scope, spirit, function and effectiveness of the invention. Among the many preferred four-component formulations are those wherein the anticonvulsant is gabapentin, the neurosteroidal agent is progesterone, the NK-1 receptor antagonist is aprepitant, and the lithium-containing compound is lithium carbonate.

Preferred dosages of the respective compounds are many, and include any that produce the required or desired effect with respect to the particular trauma or traumas. As one of skill in the art can appreciate, such dosages can be tailored with respect to many factors. Exemplary of these factors are the nature and extent of the trauma, the cause of the trauma, the tissues affected by the trauma, the time since the traumatic event, whether the traumatic event is continuing or ongoing, the current medications being taken by the subject, if any, the standard or other emergency medical procedures being applied to the subject at the time, the proximity to, need for, and range of care of a specialized healthcare facility, such as a hospital or emergency clinic, as well as the size, gender, race, ethnicity, age and physical condition of the subject mammal, especially humans.

As one of skill in the art will comprehend, the formulations of the invention described herein include those wherein one of the four compounds can be provided in a number of ranges, while the relative amounts the remaining three components of the invention in the specified ranges can be determined by methods known generally in the pharmaceutical art.

Among these formulations wherein the range amount of one component is defined are those wherein the gabapentin is provided in specified dosage ranges. As examples of preferred ranges of gabapentin, a dosage range of from about 5.0 mg to about 9,600 mg. is provided. Similarly, a preferred dosage range of the gabapentin component can be provided in a dosage range of from about 50 mg to about 4,800 mg. A more preferred dosage range is where the gabapentin is provided in a dosage range of from about 100 mg to about 2,400 mg. In a most preferred dosage range the gabapentin can be provided in a dosage range of from about 200 mg to about 600 mg. Yet other preferred formulations of the invention include wherein the gabapentin can be provided in a dosage range of from about 300 mg to about 400 mg, as well as wherein the gabapentin is provided in a dosage range of from about 325 mg to about 375 mg.

Similarly, among these formulations are those wherein the progesterone is provided in set dosage ranges while the amounts of the other components are determined relative to those ranges. Exemplary of these are wherein the progesterone is provided in amounts of from about 5.0 mg to about 1,200 mg. In another preferred dosage range, the progesterone is provided in a range of from about 5 mg to about 600 mg. A more preferred dosage range is where the progesterone is provided in a dosage range of from about 50 mg to about 450 mg. In a most preferred dosage range the progesterone is provided in a dosage range of from about 100 mg to about 300 mg. Yet other preferred formulations of the invention include wherein the progesterone is provided in a dosage of from about 150 mg to about 250 mg, as well as wherein the progesterone is provided in a dosage range of from about 190 mg to about 230 mg.

This same principle pertains to the components aprepitant and lithium-containing compounds of the formulations of the invention. Among these formulations are those wherein the aprepitant is provided in a preferable dosage range of from about 0.05 mg to about 750 mg. In a more preferred dosage range the aprepitant is provided in a dosage range of from about 5 mg to about 375 mg. An even more preferred dosage range is where the aprepitant is provided in a dosage range of from about 20 mg to about 250 mg. Moreover, in a most preferred dosage range, the aprepitant is provided in a dosage range of from about 40 mg to about 120 mg. Yet other most preferred formulations of the invention include wherein the aprepitant is provided in a dosage range of from about 60 mg to about 100 mg as well as wherein the aprepitant is provided in a dosage range of from about 70 mg to about 90 mg.

With respect to lithium-containing compounds, among the formulations that are initially defined by one component are those wherein the lithium carbonate is provided in a preferred dosage range of from about 3.0 to about 3,600 mg. In a more preferred dosage range the lithium carbonate is provided in a dosage range of from about 30 mg to about 1,800 mg. A more preferred dosage range is where the aprepitant is provided in a dosage range of from about 20 mg to about 250 mg. In a most preferred dosage range the lithium carbonate is provided in a dosage range of from about 200 mg to about 600 mg. Yet other preferred formulations of the invention include wherein the lithium carbonate is provided in a dosage range of from about 300 mg to about 500 mg as well as wherein the lithium carbonate is provided in a dosage range of from about 350 mg to about 450 mg.

Particular Four-component Formulations

As yet another advantage of the invention, many preferred four-component formulations of the invention are provided wherein each of the four components is provided in a specified range. Among these preferred formulations are those wherein the gabapentin is provided in a dosage range of from about 5.0 mg to about 9,600 mg, wherein the progesterone is provided in a dosage range of from about 5.0 mg to about 1,200 mg, wherein the aprepitant is provided in a dosage range of from about 0.05 mg to about 750 mg, and wherein the lithium carbonate is provided in a dosage range of from about 3.0 to about 3,600 mg. Another preferred formulation comprises wherein the gabapentin is provided in a dosage range of from about 50 mg to about 4,800 mg, wherein the progesterone is provided in a dosage range of from about 5 mg to about 600 mg, wherein the aprepitant is provided in a dosage range of from about 5 mg to about 375 mg, and wherein the lithium carbonate is provided in a dosage range of from about 30 mg to about 1,800 mg.

Other preferred formulations of the invention include wherein the gabapentin is provided in a dosage range of from about 100 mg to about 2,400 mg, wherein the progesterone is provided in a dosage range of from about 50 mg to about 450 mg, wherein the aprepitant is provided in a dosage range of from about 20 mg to about 250 mg, and wherein the lithium carbonate is provided in a dosage range of from about 100 mg to about 900 mg; and wherein the gabapentin is provided in a dosage range of from about 200 mg to about 600 mg, wherein the progesterone is provided in a dosage range of from about 100 mg to about 300 mg, wherein the aprepitant is provided in a dosage range of from about 40 mg to about 120 mg, and wherein the lithium carbonate is provided in a dosage range of from about 200 mg to about 600 mg.

Yet other preferred formulations of the invention include wherein the gabapentin is provided in a dosage range of from about 300 mg to about 400 mg, wherein the progesterone is provided in a dosage range of from about 150 mg to about 250 mg, wherein the aprepitant is provided in a dosage range of from about 60 mg to about 100 mg, and wherein the lithium carbonate is provided in a dosage range of from about 300 mg to about 500 mg; as well as wherein the gabapentin is provided in a dosage range of from about 325 mg to about 375 mg, wherein the progesterone is provided in a dosage range of from about 190 mg to about 230 mg, wherein the aprepitant is provided in a dosage range of from about 70 mg to about 90 mg, and wherein the lithium carbonate is provided in a dosage range of from about 350 mg to about 450 mg.

Formulations of the invention can be provided in many types of dosages, and in many types of dosage units, including those in which the release of the individual compounds is controlled, slowed, delayed or sequenced in accordance with the desired delivery dynamics of the formulation with respect to many factors as known in the art. The many formulations of the invention can thus be adapted and arranged with respect to, as examples, the characteristics and circumstances of the subject, the nature and extent of the trauma, and the nature and extent of the overall injury. These factors include, as additional examples, the environment in which they are intended to be used, the intended users, the liquid, solid or other form in which the formulation is provided, the intended subjects or recipients, the type of trauma, the proximity and need for specialize healthcare such as a hospital or emergency clinic, the age, body weight and gender of the subject, and other medications the subject may be receiving.

In some preferred embodiments, a formulation of the invention comprises a single dosage unit. In other preferred embodiments, two, or a plurality, of dosages are provided over time with respect to the onset, or with respect to the anticipated onset, of the traumatic event. Formulations of the invention can be provided also in many types of controlled release forms adapted for providing effective amounts of each of the compounds of the formulations at appropriate times.

The various dosing regimens and timing sequences with respect to administration of the formulation can be configured such that an effective treatment for the prevention, amelioration, or post-traumatic management, of the neuropathological sequalae associated with trauma to a subject comprises the administration of one or more dosage units per day. As examples of factors to be considered in this regard, are the subject's vital signs, the subject's state of consciousness, the severity of the trauma, and other medications the subject may be taking.

In other advantageous aspects of the invention, formulations of the invention can be developed, titrated, configured, adapted and arranged with respect to one or more sets of dosage ranges for one or all of the four components or compounds of the formulation. As one example, the anticonvulsant, such as gabapentin, can be provided in a dosage range of from about 5.0 mg to about 9,600. Mg. The dosages and dosage ranges of the other three biologically active compounds can then be adapted to correspond to the chosen dosage level of the gabapentin. Thus, by using a set range for one, two or three of the four compounds of a formulation of the invention, the effectiveness of the overall formulation can be determined with respect to the chosen one, two or three compounds.

Thus, in a similar manner, the neurosteroid compound, such as progesterone, can be provided in a dosage range, for example, of from about 50 mg to about 450 mg. in order to accomplish a similar evaluation. Moreover, the NK-1 receptor antagonist, such as Aprepitant, can be provided in a dosage range of, as an example, from about 40 mg to about 120 mg, and the Lithium-containing compound of the formulation, such as lithium carbonate, can provided in a dosage range of from about 100 mg to about 900 mg.

Formulations of the invention can be provided in any effective form. As examples, formulations of the invention can be provided wherein one or more of the compounds is in the form of one or more of salts, prodrugs, hydrates, derivatives or metabolites of a compound itself, analogs, homologs, compounds acting on or through mechanisms that compounds can act on or through or compounds that modify, modulate or affect in any way pathways or processes affected by compounds or formulations of the invention.

Moreover, formulations of the invention can be provided wherein one or more of the biologically active compounds are provided in at least one controlled release form. In addition, formulations of the invention can also be adapted and arranged to be administered as one or more sustaining doses. Similarly, the disclosed formulations can be adapted and arranged to be administered before an anticipated traumatic event.

Particular Methods

In accordance with similar and parallel objectives of the invention, a method for the prevention of, for reducing the effects of, or for reducing the risk of development of neuropathology incident to trauma, is provided.

In one preferred embodiment, a method of the invention comprises the steps or actions of A) providing a formulation adapted for the prevention of the development of neuropathology, wherein the formulation comprises four biologically active compounds in amounts that are pharmaceutically effective for each compound, respectively, when administered in combination with the other three biologically active compounds, the four compounds comprising a pharmaceutically effective amount of: i) at least one biologically active compound from the group comprising anticonvulsants, ii) at least one biologically active compound from the group comprising neurosteroids; iii) at least one biologically active compound from the group comprising NK-1 receptor antagonists; and iv) at least one biologically active compound from the group comprising lithium-containing compounds, and wherein the formulation is in a form adapted and arranged for administration to a mammal in need thereof, such that the development, or the risk of development, of neuropathology is reduced, lessened, attenuated or prevented; and B) administering the formulation to a mammal in need thereof.

In accordance with a particularly advantageous aspect of the invention, Step B of the method is preferably effected with respect to time in relation to one or more of i) the onset of the trauma, ii) in anticipation of the trauma, iii) during the trauma, and iv) during a period of recovery from the trauma. A method of the invention thus affords wide choices with respect to adapting and arranging the administration of a formulation of the invention with respect to the time of the onset and duration of the trauma, as well as with respect to a possible or an expected trauma.

A method of the invention thus encompasses wherein the formulation is first administered posttraumatic event within one hour after the onset of the trauma, or within two hours after the onset of the trauma, or within three hours after the onset of the trauma, or within six hours after the onset of the trauma or within 8 hours after the onset of the trauma, or within 12 hours after the onset of the trauma, or within 18 hours after the onset of the trauma, or within 24 hours after the onset of the trauma.

In some preferred embodiments, the method of the invention includes also wherein the formulation is administered at least once when a subject is about to enter into a situation, condition or scenario where trauma may occur, in which case this is a preventive measure. Examples of such preventive administration include within 10 hours before the possible onset of the trauma, within 8 hours before the possible onset of the trauma, or within 6 hours before the possible onset of the trauma, or within 4 hours before the possible onset of the trauma, or within 2 hours before the possible onset of the trauma.

In some preferred embodiments, the method of the invention includes also wherein the formulation is administered at least once in anticipation or expectation of trauma, or prophylactically. Examples of such prophylactic administration, include within 10 hours before the expected onset or the expected end of the trauma within 8 hours before the expected onset or the expected end of the trauma, or within 6 hours before the expected onset or the expected end of the trauma, or within 4 hours before the expected onset or the expected end of the trauma, or within 2 hours before the expected onset or the expected end of the trauma.

As an additional advantageous aspect of the method of the invention, formulations of the invention can be administered more than one time. Additional administrations can be provided one or a plurality of times after the formulation is first administered regardless of whether a formulation is first administered before, during or after the trauma. In a similar manner, formulations of the invention can be administered one, or a plurality of times as desired or needed, as one or more sustaining doses in order to provide desired physiological levels in the subject of the several compounds of the formulations.

As a particularly preferred aspect of the present method, the formulation is configured such that the at least one anticonvulsant is gabapentin, the at least one neurosteroid is progesterone, the at least NK-1 receptor antagonist is aprepitant, and the at least one lithium-containing compound is lithium carbonate.

Preferred dosages of the respective formulations and compounds to be used in the present method are many, and include any that produce the required or desired effect with respect to the particular trauma or traumas. As one of skill in the art can appreciate, such dosages can be tailored with respect to many factors. Exemplary of these factors are the nature and extent of the trauma, the cause of the trauma, the tissues affected by the trauma, the time since the traumatic event, whether the traumatic event is continuing or ongoing, the current medications being taken by the subject, if any, the standard or other emergency medical procedures being applied to the subject at the time, the proximity to, need for, and range of care of a specialized healthcare facility, such as a hospital or emergency clinic, as well as the size, gender, race, ethnicity, age and physical condition of the subject mammal, especially humans.

Among these formulations are those wherein the gabapentin is provided in a dosage range of from about 5.0 mg to about 9,600 mg. In a preferred dosage range the gabapentin is provided in a dosage range of from about 50 mg to about 4,800 mg.

Among these formulations are those wherein the progesterone is provided in a dosage range of from about 5.0 mg to about 1,200 mg. In a preferred dosage range the progesterone is provided in a dosage range of from about 5 mg to about 600 mg.

Among these formulations are those wherein the aprepitant is provided in a dosage range of from about 0.05 mg to about 750 mg. In a preferred dosage range the aprepitant is provided in a dosage range of from about 5 mg to about 375 mg.

Among these formulations are those wherein the lithium carbonate is provided in a dosage range of from about 3.0 to about 3,600 mg. In a preferred dosage range the lithium carbonate is provided in a dosage range of from about 30 mg to about 1,800 mg.

Other preferred dosages of compounds and formulations suitable for use in effecting the method of the invention are listed elsewhere in the present specification, both textually and in the Tables presented elsewhere in this Specification. As one of skill in the art can appreciate, any of the present formulations can be configured, adapted or arranged for use with the present method in conjunction with any of the dosage ranges of any or all of the other constituents of the formulations.

14. Scope of the Invention

The foregoing detailed description sets forth various embodiments of formulations, methods, procedures and practices for reducing or preventing the development, or the risk of development, of neuropathology as a result of traumatic injury. Insofar as such formulations, methods, procedures and practices contain one or more functions or operations, it will be understood by those within the art that each formulation, method, procedure and practice can be implemented, individually or collectively, within a wide range of many combinations without undue experimentation.

A person having ordinary skill in the art will recognize that, in one significant aspect, the herein described formulations (e.g., any combination of any two, any three or all four of gabapentin, progesterone, aprepitant and lithium), methods, and procedures and practices, and the discussion accompanying them, are used as examples for the sake of conceptual clarity and that various methods, procedures and practices are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific formulation components (e.g., gabapentin, progesterone, aprepitant and lithium), methods, and procedures and practices herein should not be taken as indicating that limitation is desired.

It is generally contemplated that the formulations according to the inventive subject matter will be formulated for administration to a mammal, and especially to a human, having a condition that is responsive to the administration of such a formulation. Therefore, where contemplated formulation compounds are administered in a pharmacological composition, it is understood that contemplated compounds can be formulated in admixture with pharmaceutically acceptable carriers. As an example but not exclusively, contemplated compounds can be administered orally as pharmacologically acceptable salts, or intravenously in a physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the present disclosure to provide numerous formulations for a particular route of administration.

In particular, contemplated compounds may be modified to render them more soluble in water or other vehicle that, for example, may be easily accomplished with minor modifications (e.g. salt formulation, esterification, etc.) that are well within the ordinary skill in the art. It is also well within the ordinary skill of the art to modify the route of administration and dosage regimen of a particular compound or formulation in order to manage the pharmacokinetics of the present compounds for maximum beneficial effect in a patient or subject.

In particular, contemplated compounds may be prepared for delivery in tablet, capsule, pill or solution form, including any form that can deliver a controlled release of these compounds.

Similarly, it should be appreciated that while some claims recite components of formulations of invention embodiments, one of skill in the art will comprehend that other constituents, while pharmacologically inactive or inert in the context of the presently disclosed technology, might be a part of the formulation. Such inactive constituents include, as examples, excipients, binders, coatings, absorption enhancers, penetration enhancers, transport enhancers, stabilizers, chelators, buffers, carriers, clearance modifiers, emulsifying agents, antioxidants, preservatives, sugars, salts, cellulose, dyes, flavoring agents and any other inactive ingredients that are considered generally recognized as safe.

In certain pharmaceutical dosage forms, prodrug and derivative forms of contemplated compounds may be formed for various purposes, including reduction of toxicity, increasing the organ or target cell specificity, etc. Among various prodrug and derivative forms, acylated (acetylated or other) derivatives, pyridine esters and various salt forms of the present compounds may be advantageous. One of ordinary skill in the art will recognize how to readily modify the present compounds to prodrug and other forms to facilitate delivery of active compounds to a target site within the host organism or patient. One of ordinary skill in the art will also take advantage of favorable pharmacokinetic parameters of the prodrug and other forms, where applicable, in delivering the present compounds to a targeted site within the host organism, subject or patient to maximize the intended effect of the formulation.

Similarly, it should be appreciated that contemplated compounds may also be metabolized to their biologically active form (e.g., via hydroxylation, glycosylation, oxidation etc.), and all metabolites of the compounds herein are therefore specifically contemplated. In addition, contemplated compounds (and combinations thereof) may be administered in combination with yet further antiviral and/or antibacterial agents. Suitable additional drugs therefore include but are not limited to various antibiotics (e.g., beta-lactam antibiotics, tetracycline antibiotics, oxazine antibiotics, etc.), various antiviral compounds (e.g., polymerase inhibitors), and/or compounds that stimulate the immune system.

With the presently disclosed technology described in detail herein, it is to be understood that the invention is not limited to the particular embodiments described, as such may, of course, vary. It is also to be understood that the terminology used herein is for the purpose of describing particular embodiments, and is not intended to be limiting, since the scope of the presently disclosed technology will be limited only by the appended claims or by a fair reading of the application as a whole.

Where a range of values is provided, it is understood that each intervening value, to the tenth of the unit of the lower limit unless the context clearly dictates otherwise, between the upper and lower limit of that range and any other stated or intervening value in that stated range is encompassed within embodiments of the invention. The upper and lower limits of these smaller ranges may independently be included in the smaller ranges is also encompassed within embodiments of the invention, subject to any specifically excluded limit in the stated range. Where the stated range includes one or both of the limits, ranges excluding either or both of those included limits are also included in embodiments of the invention.

Unless defined otherwise, all technical and scientific terms used herein have the same meaning as commonly understood by one of ordinary skill in the art to which embodiments of this invention belongs. Although any methods and materials similar or equivalent to those described herein can also be used in the practice or testing of the presently disclosed technology, a limited number of the exemplary methods and materials are described herein.

All publications mentioned herein are hereby incorporated by reference to disclose and describe the methods and/or materials in connection with which the publications are cited, as well as the general background for the inventive subject matter disclosed herein. The publications discussed herein are provided solely for their disclosure prior to the filing date of the present application. Nothing herein is to be construed as an admission that the presently disclosed technology is not entitled to antedate such publication by virtue of prior invention. Further, the dates of publication provided might be different from the actual publication dates, which may need to be independently confirmed.

The inventive technology described herein sometimes illustrates different components contained within, or connected with, different other components. It is to be understood that such descriptions or subject matter are merely exemplary, and that in fact many other descriptions, examples, methods, procedures and practices can be implemented which achieve the same functionality. In a conceptual sense, any arrangement of components to achieve the same functionality is effectively "associated" or "coupled" such that the desired functionality is achieved. Hence, any two or more methods, procedures or practices herein combined to achieve a particular functionality can be seen as "associated with" each other such that the desired functionality is achieved, irrespective of condition, event, injury, damage or pathology components. Likewise, any two or more components so associated can also be viewed as being "operably connected", or "operably coupled", to each other to achieve the desired functionality, and any two or more components capable of being so associated can also be viewed as being "operably couplable", to each other to achieve the desired functionality. Specific examples of operably couplable include but are not limited to, practices of embodiments of the invention required under different conditions, practices of embodiments of invention requiring different routes or methods of administration, practices of embodiments of invention requiring repeated administration for varying periods of time or logically interacting or logically interactable components to achieve the desired functionality.

In a general sense, those skilled in the art will recognize that the various aspects described herein which could be implemented, individually or collectively, by a wide range of methods, procedures or practices, or any combination thereof, can be viewed as being composed of various types of "formulation." Consequently, as used herein "formulation" includes, but is not limited to, two compounds selected from gabapentin, progesterone, aprepitant and lithium, three compounds selected from gabapentin, progesterone, aprepitant and lithium or all four compounds selected from gabapentin, progesterone, aprepitant and lithium. Those having skill in the art will recognize that the subject matter described herein may be implemented in a method, procedure or practice as described herein, or some combination thereof.

As examples, the formulations, methods, procedures or practices of certain embodiments of the invention include many combinations and permutations thereof with respect to the nature of the individual formulations, and their relative methods, procedures or practices, can vary in operation by the relative methods, procedures or practices.

While particular aspects of the present subject matter described herein have been shown and described, it will be apparent to those skilled in the art that, based upon the embodiments herein, changes and modifications may be made without departing from the subject matter described herein and its broader aspects and, therefore, the appended claims are to encompass within their scope all such changes and modifications as are within the true spirit and scope of the subject matter described herein.

Those skilled in the art will recognize that it is common within the art to describe methods, procedures or practices in the fashion set forth herein, and thereafter use standard practices to integrate such described methods, processes or procedures to reduce or prevent the development or the risk of development of neuropathology as a result of traumatic injury. That is, at least a portion of the methods, procedures or practices described herein can be integrated into reducing or preventing the development or the risk of development of neuropathology as a result of traumatic injury via a reasonable amount of experimentation. Those having skill in the art will recognize that typical methods, procedures or practices generally include those described herein. A typical method, procedure or practice may be implemented utilizing any suitable commercially available instrument, tool or device, such as any typically found in a medical facility or health delivery context or venue, and available to those typically familiar with methods, procedures or practices generally applied by those skilled in the art.

With respect to the use of substantially any plural or singular terms herein, those having skill in the art can translate from the plural to the singular or from the singular to the plural as is appropriate to the context or application. The various singular/plural permutations are not expressly set forth herein for sake of clarity.

Furthermore, it is to be understood that the invention is defined by the appended claims, and by the many claims that could be supported by the present specification. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" or "an" should typically be interpreted to mean "at least one" or "one or more"); the same holds true for the use of definite articles used to introduce claim recitations.

It will be further understood by those within the art that virtually any disjunctive word or phrase presenting two or more alternative terms, whether in the description, claims, or practices, should be understood to contemplate the possibilities of including one of the terms, either of the terms, or both terms. It is also to be understood that the terminology employed in the Detailed Description sections of this application is for the purpose of describing particular embodiments. It is also contemplated that any optional feature of the inventive variations described herein may be set forth and claimed independently, or in combination with any one or more of the features described herein. Moreover, in interpreting the disclosure, all terms should be interpreted in the broadest possible manner consistent with the context of the disclosed technology. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Thus, many specific compositions and methods of "Formulations, Procedures, Methods And Combinations Thereof For Reducing Or Preventing The Development, Or The Risk Of Development, Of Neuropathology As A Result Of Traumatic Injury" have been disclosed and exemplified. It should be apparent, however, to those skilled in the art that many more modifications besides those already described are possible without departing from the inventive concepts herein, or from the spirit of the invention. The inventive subject matter, therefore, is not to be restricted except in the spirit of the disclosure.

What is claimed is:

1. A formulation adapted for the prophylactic treatment of neuropathology caused by trauma to a subject, or for the amelioration of the effects caused by trauma to a subject, the formulation comprising at least one compound of each of A, B, C, and D below, in amounts that are pharmaceutically effective for each compound, respectively, when administered in combination with the other compounds, the formulation comprising a pharmaceutically effective amount of:

A) at least one compound from the group comprising anticonvulsants and antiepileptics, wherein the compound is one or more of gabapentin, pregabalin and valproic acid, wherein, when gabapentin is included in the formulation, it is provided in a dosage range of from about 5.0 mg to about 9,600 mg; wherein when pregabalin is included in the formulation, it is provided in a dosage range of from about 0.5 mg to about 2,400 mg, and wherein when valproic acid is included in the formulation, it is provided in a dosage range of from about 25 mg to about 8,400 mg;

B) at least one compound from the group comprising neurosteroids, neuroactive steroids and progestins, wherein the compound comprises methylprednisolone and optionally one or more of megestrol acetate and ganaxolone, wherein, the methylprednisolone is included in the formulation in a dosage range of from about 0.02 mg to 500 mg;

C) at least one compound from the group comprising NK-1 receptor antagonists, wherein the compound comprises aprepitant and optionally one or more of vestipitant and casopitant, wherein, the aprepitant is included in the formulation in a dosage range of from about 0.05 mg to about 750 mg, when vestipitant is included in the formulation, it is provided in a dosage range of from about 0.001 mg to about 200 mg, and when casopitant is included in the formulation, it is provided in a dosage range of from about 0.005 mg to about 1,000 mg; and D) at least one compound from the group comprising lithium-containing compounds, wherein the lithium-containing compound is one or more of lithium carbonate, lithium citrate and lithium chloride, and wherein, when lithium carbonate is included in the formulation, it is provided in a dosage range of from about 0.5 mg to about 3,600 mg, when lithium citrate is included in the formulation, it is provided in a dosage range of from about 0.01 mg to about 2,400 mg, and when lithium chloride is included in the formulation, it is provided in a dosage range of from about 3 mg to about 3,600 mg, wherein the formulation is in a form and a dosage with respect to each of its components such that it is adapted and arranged for administration to a mammal in need thereof, such that the development, or the risk of development, of neuropathology caused by trauma to a subject, or for the effects caused by trauma to a subject, are reduced, lessened, attenuated or prophylactically treated, and wherein the formulation is provided in a single dosage unit.

2. The formulation of claim 1, wherein the anticonvulsant and antiepileptic is gabapentin, and wherein the gabapentin is provided in a dosage range of from about 50 mg to about 4,800 mg, in a dosage range of from about 100 mg to about 2,400 mg, or in a dosage range of from about 200 mg to about 600 mg.

3. The formulation of claim 1, wherein the anticonvulsant and antiepileptic is pregabalin, and wherein the pregabalin is provided in a dosage range of from about 15 mg to about 1,200 mg, in a dosage range of from about 25 mg to about 600 mg., or in a dosage range of from about 50 mg to about 150 mg.

4. The formulation of claim 1, wherein the anticonvulsant and antiepileptic is valproic acid, and wherein the valproic acid is provided in a dosage range of from about 250 mg to about 4,200 mg, in a dosage range of from about 750 mg to about 3,750 mg, or in a dosage range of from about 1,000 mg to about 3,000 mg.

5. The formulation of claim 1, wherein the compound selected from the group comprising neurosteroids, neuroactive steroids and progestins, comprises megestrol acetate (17-Hydroxy-6-methylpregna-3,6-diene-3,20-dione).

6. The formulation of claim 1, wherein the NK-1 receptor antagonist is aprepitant, and the aprepitant is provided in a dosage range of from about 5 mg to about 375 mg, in a dosage range of from about 20 mg to about 250 mg, or a dosage range of from about 40 mg to about 120 mg.

7. The formulation of claim 1, wherein the NK-1 receptor antagonist comprises vestipitant, and the vestipitant is provided in a dosage range of from about 1 mg to about 100 mg, in a dosage range of from about 1 mg to about 60 mg, or a dosage range of from about 5 mg to about 15 mg.

8. The formulation of claim 1, wherein the NK-1 receptor antagonist comprises casopitant, and the casopitant is provided in a dosage range of from about 0.5 mg to about 500 mg, in a dosage range of from about 10 mg to about 300 mg, or a dosage range of from about 50 mg to about 150 mg.

9. The formulation of claim 1, wherein the lithium-containing compound is lithium carbonate, and is provided in a dosage range of from about 30 mg to about 1,800 mg, in a dosage range of from about 100 mg to about 900 mg, or a dosage range of from about 200 mg to about 600 mg.

10. The formulation of claim 1, wherein the lithium-containing compound is lithium citrate and the lithium citrate is provided in a dosage range of from about 10 mg to about 1,200 mg, in a dosage range of from about 50 mg to about 900 mg, or a dosage range of from about 200 mg to about 600 mg.

11. The formulation of claim 1, wherein the lithium-containing compound is lithium chloride and the lithium chloride is provided in a dosage range of from about 30 mg to about 1,800 mg, in a dosage range of from about 100 mg to about 900 mg, or in a dosage range of from about 200 mg to about 600 mg.

12. The formulation of claim 1, wherein an effective treatment level for the prophylactic treatment of neuropathology caused by trauma to a subject or the effects of trauma to a subject comprises an administration of one or more dosage units per day.

13. The formulation of claim 1, wherein administration is performed with respect to time in relation to one or more of i) the onset of the trauma, ii) in anticipation of the trauma, iii) during the trauma, and iv) during a period of recovery from the trauma.

14. The formulation of claim 1, wherein administration is first performed within two (2) hours after the onset or end of a trauma.

15. The formulation of claim 1, wherein administration is first performed within twenty-four (24) hours after the onset or end of a trauma.

16. The formulation of claim 1, wherein administration is first performed prophylactically within six (6) hours before the expected onset or the expected end of a trauma.

17. The formulation of claim 1, wherein administration is performed additionally one, or a plurality of, times after the formulation is first administered.

18. The formulation of claim 1, wherein administration is performed one, or a plurality of times as a sustaining dose as needed.

19. The formulation of claim 1, wherein the compound selected from the group comprising neurosteroids, neuroactive steroids and progestins comprises ganaxolone (3α-hydroxy-3β-methyl-5α-pregnan-20-one).

20. The formulation of claim 1, wherein the compound selected from the group comprising neurosteroids, neuroactive steroids and progestins is methylprednisolone sodium succinate, and is provided in a dosage range of from about 2 mg to about 250 mg, in a dosage range of from about 10 mg to about 80 mg, or in a dosage range of from about 15 mg to about 45 mg.

21. A method for the prophylactic treatment of neuropathology caused by trauma to a subject, or for the amelioration of the effects caused by trauma to a subject, the method comprising the steps or actions of:
A) providing a formulation comprising at least one compound from each of a), b), c) and d) below in amounts that are pharmaceutically effective for each compound, respectively, when administered in combination with the other compounds, the formulation comprising a pharmaceutically effective amount of:
a) at least one compound from the group comprising anticonvulsants and antiepileptics, wherein the compound is one or more of gabapentin, pregabalin and valproic acid, wherein, when gabapentin is included in the formulation, it is provided in a dosage range of from about 5.0 mg to about 9,600 mg; wherein when pregabalin is included in the formulation, it is provided in a dosage range of from about 0.5 mg to about 2,400 mg, and wherein when valproic acid is included in the formulation, it is provided in a dosage range of from about 25 mg to about 8,400 mg;
b) at least one compound from the group comprising neurosteroids, neuroactive steroids and progestins, wherein the compound comprises methylprednisolone and optionally one or more of megestrol acetate and ganaxolone, wherein, the methylprednisolone is included in the formulation in a dosage range of from about 0.02 mg to 500 mg;
c) at least one compound from the group comprising NK-1 receptor antagonists wherein the compound is aprepitant, and optionally one or more of vestipitant and casopitant, wherein, aprepitant is provided in a dosage range of from about 0.05 mg to 750 mg, when vestipitant is included in the formulation, it is provided in a dosage range of from about 0.001 mg to about 200 mg, and when casopitant is included in the formulation, it is provided in a dosage range of from about 0.005 mg to 1,000 mg, and d) at least one compound from the group comprising lithium-containing compounds, wherein the lithium-containing compound is one or more of lithium carbonate, lithium citrate and lithium chloride, and wherein, when lithium carbonate is included in the formulation, it is provided in a dosage range of from about 0.5 mg to about 3,600 mg; when lithium citrate is included in the formulation, it is provided in a dosage range of from about 0.01 mg to about 2,400 mg, and when lithium chloride is included in the formulation, it is provided in a dosage range of from about 3 mg to about 3,600 mg; and wherein the formulation is in a form and a dosage with respect to each of its components such that it is adapted and arranged for administration to a mammal in need thereof, such that the development, or the risk of development, of neuropathology caused by trauma to a subject, or for the effects caused by trauma to a subject, are reduced, lessened, attenuated or prophylactically treated, and wherein the formulation is provided in a single dosage unit; and B) administering the formulation to a mammal in need thereof.

22. The method of claim 21, wherein Step B is effected with respect to time in relation to one or more of a) the onset of the trauma, b) in anticipation of the trauma, c) during the trauma, and d) during a period of recovery from the trauma.

23. The method of claim 21, wherein the at least one anticonvulsant and antiepileptic is gabapentin and wherein the gabapentin is provided in a dosage range of from about 50 mg to about 4,800 mg, in a dosage range of from about 100 mg to about 2,400 mg, or in a dosage range of from about 200 mg to about 600 mg.

24. The method of claim 21, wherein the at least one anticonvulsant and antiepileptic is pregabalin, and wherein the pregabalin is provided in a dosage range of from about 15 mg to about 1,200 mg, in a dosage range of from about 25 mg to about 600 mg, or in a dosage range of from about 50 mg to about 150 mg.

25. The method of claim 21, wherein the at least one anticonvulsant and antiepileptic is valproic acid, and wherein the valproic acid is provided in a dosage range of from about 250 mg to about 4,200 mg, in a dosage range of from about 750 mg to about 3,750 mg, or in a dosage range of from about 1,000 mg to about 3,000 mg.

26. The method of claim 21, wherein the at least one neurosteroid, neuroactive steroid and progestin comprises megestrol acetate.

27. The method of claim 21, wherein the at least one neurosteroid, neuroactive steroid and progestin comprises ganaxolone (3α-hydroxy-3β-methyl-5α-pregnan-20-one).

28. The method of claim 21, wherein the at least one neurosteroid, neuroactive steroid and progestin, is methylprednisolone sodium succinate, and is provided in a dosage range of from about 2 mg to about 250 mg, in a dosage range of from about 10 mg to about 80 mg, or in a dosage range of from about 15 mg to about 45 mg.

29. The method of claim 21, wherein the at least one NK-1 receptor antagonist is aprepitant, and the aprepitant is provided in a dosage range of from about 5 mg to about 375 mg, in a dosage range of from about 20 mg to about 250 mg, or a dosage range of from about 40 mg to about 120 mg.

30. The method of claim 21, wherein the at least one NK-1 receptor antagonist comprises vestipitant, and the vestipitant is provided in a dosage range of from about 1 mg to about 100 mg, in a dosage range of from about 1 mg to about 60 mg, or a dosage range of from about 5 mg to about 15 mg.

31. The method of claim 21, wherein the at least one NK-1 receptor antagonist comprises casopitant, and the casopitant is provided in a dosage range of from about 0.5 mg to about 500 mg, in a dosage range of from about 10 mg to about 300 mg, or a dosage range of from about 50 mg to about 150 mg.

32. The method of claim 21, wherein the at least one lithium-containing compound is lithium carbonate, and the lithium carbonate is provided in a dosage range of from about 30 mg to about 1,800 mg, in a dosage range of from about 100 mg to about 900 mg, or a dosage range of from about 200 mg to about 600 mg.

33. The method of claim 21, wherein the at least one lithium-containing compound is lithium citrate and is provided in a dosage range of from about 10 to about 1,200 mg, in a dosage range of from about 50 to about 900 mg, or a dosage range of from about 200 to about 600 mg.

34. The method of claim 21, wherein the at least one lithium-containing compound is lithium chloride and is provided in a dosage range of from about 30 to about 1,800 mg, in a dosage range of from about 100 to about 900 mg, or in a dosage range of from about 200 to about 600 mg.

35. The method of claim 21, wherein the formulation is first administered within two hours after the trauma.

36. The method of claim 21, wherein the formulation is first administered prophylactically within 6 hours before the expected onset or the expected end of the trauma.

37. The method of claim 21, wherein the formulation is administered additionally one, or a plurality of, times after the formulation is first administered.

38. The method of claim 21, wherein the formulation is administered one, or a plurality of times as a sustaining dose as needed.

39. The formulation of claim 1, wherein the compound selected from the group comprising neurosteroids, neuroactive steroids and progestins comprises ganaxolone (3α-hydroxy-3β-methyl-5α-pregnan-20-one).

40. The method of claim 21, wherein the formulation is first administered within 24 hours alter the trauma.

41. The method of claim 21, wherein the formulation is administered one, or a plurality of times as a sustaining dose as needed.

* * * * *